United States Patent
Bedenbaugh

(10) Patent No.: US 8,849,415 B2
(45) Date of Patent: Sep. 30, 2014

(54) MULTI-CHANNEL CONNECTOR FOR BRAIN STIMULATION SYSTEM

(75) Inventor: Purvis Bedenbaugh, Tampa, FL (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 830 days.

(21) Appl. No.: 13/082,906

(22) Filed: Apr. 8, 2011

(65) Prior Publication Data

US 2011/0184335 A1 Jul. 28, 2011

Related U.S. Application Data

(60) Continuation of application No. 12/509,096, filed on Jul. 24, 2009, now Pat. No. 7,945,329, which is a division of application No. 11/830,565, filed on Jul. 30, 2007, now Pat. No. 7,583,999.

(60) Provisional application No. 60/820,914, filed on Jul. 31, 2006.

(51) Int. Cl.
| | |
|---|---|
| *A61N 1/05* | (2006.01) |
| *H01R 13/621* | (2006.01) |
| *H01R 13/24* | (2006.01) |
| *H01R 24/58* | (2011.01) |
| *H01R 13/64* | (2006.01) |
| *H01R 4/36* | (2006.01) |
| *H01R 107/00* | (2006.01) |

(52) U.S. Cl.
CPC ............ *H01R 13/64* (2013.01); *H01R 13/6215* (2013.01); *H01R 13/2407* (2013.01); *H01R 24/58* (2013.01); *H01R 2107/00* (2013.01); *H01R 13/2435* (2013.01); *H01R 2201/12* (2013.01); *A61N 1/0529* (2013.01); *H01R 4/363* (2013.01); *A61N 1/0539* (2013.01); *A61B 2562/227* (2013.01)
USPC .............. 607/115; 607/37; 607/116; 607/118

(58) Field of Classification Search
CPC ... A61N 1/3752; A61N 1/375; A61N 1/0539; A61N 1/3754; A61N 1/02; A61N 1/36017; A61N 2001/083; A61N 1/00; A61N 1/0476; A61N 1/0558; A61N 1/057; H01R 2201/12; H01R 13/506; H01R 43/20; A61B 2562/0209; Y10S 439/909; H04B 13/005
USPC .................................... 607/37, 115–116, 118
See application file for complete search history.

(56) References Cited

U.S. PATENT DOCUMENTS

| | | | |
|---|---|---|---|
| 3,908,668 | A | 9/1975 | Bolduc |
| 3,951,154 | A | 4/1976 | Hartlaub |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

Baldi et al., "A Microstructured Silicon Membrane with Entrapped Hydrogels for Environmentally Sensitive Fluid Gating," Sensor and Actuators B, 114(1):9-18, 2006.

(Continued)

*Primary Examiner* — Deborah Malamud
(74) *Attorney, Agent, or Firm* — Lowe Graham Jones PLLC; Bruce E. Black

(57) ABSTRACT

An implantable connector for use with a neurological device and a lead extension includes a male connector having a plurality of electrical contacts axially arranged along the connector, insulated from each other. The connector also includes a female connector having one or more channels axially disposed therein and a plurality of conductors axially arranged on the female connector. The plurality of conductors are electrically insulated from each other, and at least one indexing element is disposed adjacent to one or more of the channels. The indexing element allows the male connector to be received into the one or more channels in a defined orientation relative to the channel, thereby forming at least two electrical connections along two or more axial positions. Often the neurological device is a brain stimulating and recording lead. The male and female connectors are often fastened together with a screw or by twist-locking the two members together.

18 Claims, 20 Drawing Sheets

(56) References Cited

U.S. PATENT DOCUMENTS

| | | |
|---|---|---|
| 3,990,727 A | 11/1976 | Gallagher |
| 4,236,525 A | 12/1980 | Sluetz et al. |
| 4,328,813 A | 5/1982 | Ray |
| 4,350,159 A | 9/1982 | Gouda |
| 4,437,474 A | 3/1984 | Peers-Trevarton |
| 4,458,677 A | 7/1984 | McCorkle, Jr. |
| 4,471,777 A | 9/1984 | McCorkle, Jr. |
| 4,565,200 A | 1/1986 | Cosman |
| 4,602,624 A | 7/1986 | Naples et al. |
| 4,603,696 A | 8/1986 | Cross, Jr. et al. |
| 4,630,611 A | 12/1986 | King |
| 4,712,557 A | 12/1987 | Harris |
| 4,736,999 A | 4/1988 | Marks et al. |
| 4,744,370 A | 5/1988 | Harris |
| 4,784,141 A | 11/1988 | Peers-Trevarton |
| 4,832,032 A | 5/1989 | Schneider |
| 4,886,065 A | 12/1989 | Collins, Jr. |
| 4,931,056 A | 6/1990 | Ghajar et al. |
| 4,934,366 A | 6/1990 | Truex et al. |
| 4,955,891 A | 9/1990 | Carol |
| 5,000,194 A | 3/1991 | van den Honert et al. |
| 5,006,122 A | 4/1991 | Wyatt et al. |
| 5,036,862 A | 8/1991 | Pohndorf |
| 5,116,345 A | 5/1992 | Jewell et al. |
| 5,119,832 A | 6/1992 | Xavier |
| 5,135,001 A | 8/1992 | Sinofsky et al. |
| 5,246,014 A | 9/1993 | Williams et al. |
| 5,257,622 A | 11/1993 | Hooper et al. |
| 5,300,080 A | 4/1994 | Clayman et al. |
| 5,318,041 A | 6/1994 | DuBois et al. |
| 5,330,485 A | 7/1994 | Clayman et al. |
| 5,374,279 A | 12/1994 | Duffin, Jr. et al. |
| 5,374,285 A | 12/1994 | Vaiani et al. |
| 5,439,391 A | 8/1995 | McEtchin et al. |
| 5,458,629 A | 10/1995 | Baudino et al. |
| 5,462,545 A | 10/1995 | Wang et al. |
| 5,464,446 A | 11/1995 | Dreessen et al. |
| 5,522,874 A | 6/1996 | Gates |
| 5,618,287 A | 4/1997 | Fogarty et al. |
| 5,683,422 A | 11/1997 | Rise |
| 5,711,316 A | 1/1998 | Elsberry et al. |
| 5,713,922 A | 2/1998 | King |
| 5,716,377 A | 2/1998 | Rise |
| 5,752,937 A | 5/1998 | Otten et al. |
| 5,800,350 A | 9/1998 | Coppleson et al. |
| 5,843,141 A | 12/1998 | Bischoff et al. |
| 5,843,148 A | 12/1998 | Gijsbers et al. |
| 5,897,585 A | 4/1999 | Williams |
| 5,906,634 A | 5/1999 | Flynn et al. |
| 5,925,073 A | 7/1999 | Chastain et al. |
| 5,935,159 A | 8/1999 | Cross, Jr. et al. |
| 5,938,688 A | 8/1999 | Schiff |
| 5,968,082 A | 10/1999 | Heil |
| 5,987,361 A | 11/1999 | Mortimer |
| 6,006,135 A | 12/1999 | Kast et al. |
| 6,011,996 A | 1/2000 | Gielen et al. |
| 6,018,684 A | 1/2000 | Bartig et al. |
| 6,026,567 A | 2/2000 | Swoyer et al. |
| 6,038,480 A | 3/2000 | Hrdlicka et al. |
| 6,044,304 A | 3/2000 | Baudino |
| 6,066,165 A | 5/2000 | Racz |
| 6,094,598 A | 7/2000 | Elsberry et al. |
| 6,134,478 A | 10/2000 | Spehr |
| 6,161,047 A | 12/2000 | King et al. |
| 6,167,311 A | 12/2000 | Rezai |
| 6,167,314 A | 12/2000 | Fischer, Sr. et al. |
| 6,181,969 B1 | 1/2001 | Gord |
| 6,181,971 B1 | 1/2001 | Doan |
| 6,205,358 B1 | 3/2001 | Haeg et al. |
| 6,227,203 B1 | 5/2001 | Rise et al. |
| 6,249,708 B1 | 6/2001 | Nelson et al. |
| 6,261,300 B1 | 7/2001 | Carol et al. |
| 6,301,492 B1 | 10/2001 | Zonenshayn |
| 6,321,126 B1 | 11/2001 | Kuzma |
| 6,322,559 B1 | 11/2001 | Daulton et al. |
| 6,343,226 B1 | 1/2002 | Sunde et al. |
| 6,356,792 B1 | 3/2002 | Errico et al. |
| 6,370,434 B1 | 4/2002 | Zhang et al. |
| 6,413,263 B1 | 7/2002 | Lobdill et al. |
| 6,416,520 B1 | 7/2002 | Kynast et al. |
| 6,428,368 B1 | 8/2002 | Hawkins et al. |
| 6,430,442 B1 | 8/2002 | Peters et al. |
| 6,456,869 B1 | 9/2002 | Raylman et al. |
| 6,456,889 B2 | 9/2002 | Pianca et al. |
| 6,456,890 B2 | 9/2002 | Pianca et al. |
| 6,475,750 B1 | 11/2002 | Han et al. |
| 6,482,182 B1 | 11/2002 | Carroll et al. |
| 6,510,347 B2 | 1/2003 | Borkan |
| 6,516,227 B1 | 2/2003 | Meadows et al. |
| 6,529,774 B1 | 3/2003 | Greene |
| 6,556,873 B1 | 4/2003 | Smits |
| 6,564,078 B1 | 5/2003 | Marino et al. |
| 6,572,624 B2 | 6/2003 | U et al. |
| 6,597,953 B2 | 7/2003 | Boling |
| 6,606,521 B2 | 8/2003 | Paspa et al. |
| 6,609,029 B1 | 8/2003 | Mann et al. |
| 6,609,032 B1 | 8/2003 | Woods et al. |
| 6,662,035 B2 | 12/2003 | Sochor |
| 6,671,534 B2 | 12/2003 | Putz |
| 6,678,564 B2 | 1/2004 | Ketterl et al. |
| 6,694,162 B2 | 2/2004 | Hartlep |
| 6,705,900 B2 | 3/2004 | Sommer et al. |
| 6,741,892 B1 | 5/2004 | Meadows et al. |
| 6,755,694 B2 | 6/2004 | Ries et al. |
| 6,757,039 B2 | 6/2004 | Ma |
| 6,757,970 B1 | 7/2004 | Kuzma et al. |
| 6,819,958 B2 | 11/2004 | Weiner et al. |
| 6,829,508 B2 | 12/2004 | Schulman et al. |
| 6,854,994 B2 | 2/2005 | Stein et al. |
| 6,878,013 B1 | 4/2005 | Behan |
| 6,895,276 B2 | 5/2005 | Kast et al. |
| 6,912,423 B2 | 6/2005 | Ley et al. |
| 6,921,295 B2 | 7/2005 | Sommer et al. |
| 6,980,863 B2 | 12/2005 | Van Venrooij et al. |
| 6,997,922 B2 | 2/2006 | Theeuwes et al. |
| 7,004,948 B1 | 2/2006 | Pianca et al. |
| 7,006,872 B2 | 2/2006 | Gielen et al. |
| 7,027,852 B2 | 4/2006 | Helland |
| 7,033,326 B1 | 4/2006 | Pianca et al. |
| 7,035,689 B1 | 4/2006 | Hawkins et al. |
| 7,047,082 B1 | 5/2006 | Schrom et al. |
| 7,047,084 B2 | 5/2006 | Erickson et al. |
| 7,051,419 B2 | 5/2006 | Schrom et al. |
| 7,069,081 B2 | 6/2006 | Biggs et al. |
| 7,092,765 B2 | 8/2006 | Geske et al. |
| 7,128,600 B2 | 10/2006 | Osypka |
| 7,146,222 B2 | 12/2006 | Boling |
| 7,177,701 B1 | 2/2007 | Pianca |
| 7,181,288 B1 | 2/2007 | Rezai et al. |
| 7,191,009 B2 | 3/2007 | Laske et al. |
| 7,225,034 B2 | 5/2007 | Ries et al. |
| 7,231,253 B2 | 6/2007 | Tidemand et al. |
| 7,241,180 B1 | 7/2007 | Rentas Torres |
| 7,242,987 B2 | 7/2007 | Holleman et al. |
| 7,244,150 B1 | 7/2007 | Brase et al. |
| 7,270,568 B2 | 9/2007 | Osypka |
| 7,271,094 B2 | 9/2007 | Conrad |
| 7,287,995 B2 | 10/2007 | Stein et al. |
| 7,292,890 B2 | 11/2007 | Whitehurst et al. |
| 7,305,267 B2 | 12/2007 | Hector |
| 7,313,442 B2 | 12/2007 | Velasco et al. |
| 7,337,005 B2 | 2/2008 | Kim et al. |
| 7,369,899 B2 | 5/2008 | Malinowski et al. |
| 7,422,487 B2 | 9/2008 | Osypka |
| 7,437,193 B2 | 10/2008 | Parramon et al. |
| 7,442,183 B2 | 10/2008 | Baudino et al. |
| 7,450,997 B1 | 11/2008 | Pianca et al. |
| 7,489,971 B1 | 2/2009 | Franz |
| 7,554,493 B1 | 6/2009 | Rahman |
| 7,583,999 B2 | 9/2009 | Bedenbaugh |
| 7,585,190 B2 | 9/2009 | Osypka |
| 7,668,601 B2 | 2/2010 | Hegland et al. |
| 7,672,734 B2 | 3/2010 | Anderson et al. |
| 7,761,165 B1 | 7/2010 | He et al. |

(56) References Cited

U.S. PATENT DOCUMENTS

| | | |
|---|---|---|
| 7,761,985 B2 | 7/2010 | Hegland et al. |
| 7,783,359 B2 | 8/2010 | Meadows |
| 7,792,590 B1 | 9/2010 | Pianca et al. |
| 7,809,446 B2 | 10/2010 | Meadows |
| 7,824,517 B2 | 11/2010 | Kampa et al. |
| 7,840,188 B2 | 11/2010 | Kurokawa |
| 7,856,707 B2 | 12/2010 | Cole |
| 7,860,570 B2 | 12/2010 | Whitehurst et al. |
| 7,945,329 B2 | 5/2011 | Bedenbaugh |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,099,177 B2 | 1/2012 | Dahlberg |
| 8,175,710 B2 | 5/2012 | He |
| 8,224,450 B2 | 7/2012 | Brase |
| 8,225,504 B2 | 7/2012 | Dye et al. |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,473,061 B2 | 6/2013 | Moffitt et al. |
| 8,504,157 B2 | 8/2013 | Barker |
| 8,548,602 B2 | 10/2013 | Moffitt et al. |
| 8,600,507 B2 | 12/2013 | Brase et al. |
| 2001/0027336 A1 | 10/2001 | Gielen et al. |
| 2001/0034543 A1 | 10/2001 | Haeg et al. |
| 2002/0115343 A1 | 8/2002 | Sommer et al. |
| 2002/0156513 A1 | 10/2002 | Borkan |
| 2002/0183817 A1 | 12/2002 | Van Venrooij et al. |
| 2003/0050549 A1 | 3/2003 | Sochor |
| 2003/0073348 A1 | 4/2003 | Ries et al. |
| 2003/0077935 A1 | 4/2003 | Stein et al. |
| 2003/0077943 A1 | 4/2003 | Osypka |
| 2003/0114905 A1 | 6/2003 | Kuzma |
| 2003/0120328 A1 | 6/2003 | Jenkins et al. |
| 2003/0143895 A1 | 7/2003 | Sommer et al. |
| 2003/0163171 A1 | 8/2003 | Kast et al. |
| 2003/0231266 A1 | 12/2003 | Ma |
| 2004/0015205 A1 | 1/2004 | Whitehurst et al. |
| 2004/0039434 A1 | 2/2004 | Schrom et al. |
| 2004/0059348 A1 | 3/2004 | Geske et al. |
| 2004/0059392 A1 | 3/2004 | Parramon et al. |
| 2004/0064164 A1 | 4/2004 | Ries et al. |
| 2004/0116977 A1 | 6/2004 | Finch et al. |
| 2004/0122481 A1 | 6/2004 | Tidemand et al. |
| 2004/0215282 A1 | 10/2004 | Weijden et al. |
| 2004/0215303 A1 | 10/2004 | Sage |
| 2004/0230268 A1 | 11/2004 | Huff et al. |
| 2004/0260355 A1 | 12/2004 | Holleman et al. |
| 2004/0260373 A1 | 12/2004 | Ries et al. |
| 2004/0267284 A1 | 12/2004 | Parmer et al. |
| 2005/0015130 A1 | 1/2005 | Gill |
| 2005/0027326 A1 | 2/2005 | Ries et al. |
| 2005/0033371 A1 | 2/2005 | Sommer et al. |
| 2005/0043770 A1 | 2/2005 | Hine et al. |
| 2005/0043771 A1 | 2/2005 | Sommer et al. |
| 2005/0065570 A1 | 3/2005 | Stein et al. |
| 2005/0131483 A1 | 6/2005 | Zhao et al. |
| 2005/0165465 A1 | 7/2005 | Pianca et al. |
| 2005/0171509 A1 | 8/2005 | Hector |
| 2005/0171587 A1 | 8/2005 | Daglow et al. |
| 2005/0182464 A1 | 8/2005 | Schulte et al. |
| 2005/0186829 A1 | 8/2005 | Balsells |
| 2005/0192594 A1 | 9/2005 | Skakoon et al. |
| 2005/0222642 A1 | 10/2005 | Przybyszewski et al. |
| 2005/0272280 A1 | 12/2005 | Osypka |
| 2006/0004422 A1 | 1/2006 | De Ridder |
| 2006/0015163 A1 | 1/2006 | Brown |
| 2006/0025841 A1 | 2/2006 | McIntyre |
| 2006/0041293 A1 | 2/2006 | Mehdizadeh et al. |
| 2006/0047325 A1 | 3/2006 | Thimineur et al. |
| 2006/0166563 A1 | 7/2006 | Osypka |
| 2006/0167522 A1 | 7/2006 | Malinowski |
| 2006/0247697 A1 | 11/2006 | Sharma et al. |
| 2006/0259106 A1 | 11/2006 | Arnholt et al. |
| 2007/0099487 A1 | 5/2007 | Osypka |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0178770 A1 | 8/2007 | Rentas Torres |
| 2007/0203546 A1 | 8/2007 | Stone et al. |
| 2007/0219595 A1 | 9/2007 | He |
| 2007/0239243 A1 | 10/2007 | Moffitt et al. |
| 2008/0027504 A1 | 1/2008 | Bedenbaugh |
| 2008/0039900 A1 | 2/2008 | Stein et al. |
| 2008/0071320 A1 | 3/2008 | Brase |
| 2008/0103580 A1 | 5/2008 | Gerber |
| 2008/0114230 A1 | 5/2008 | Addis |
| 2008/0139031 A1 | 6/2008 | Ries et al. |
| 2008/0139053 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255630 A1 | 10/2008 | Arisso et al. |
| 2008/0262564 A1 | 10/2008 | Alexander et al. |
| 2008/0274651 A1 | 11/2008 | Boyd et al. |
| 2008/0311772 A1 | 12/2008 | Osypka |
| 2009/0088826 A1 | 4/2009 | Bedenbaugh |
| 2009/0187222 A1 | 7/2009 | Barker |
| 2009/0204192 A1 | 8/2009 | Carlton et al. |
| 2009/0222073 A1 | 9/2009 | Flowers et al. |
| 2009/0233491 A1 | 9/2009 | Barker et al. |
| 2009/0259282 A1 | 10/2009 | Williams et al. |
| 2009/0264943 A1 | 10/2009 | Barker |
| 2009/0276021 A1 | 11/2009 | Meadows et al. |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094364 A1 | 4/2010 | McDonald |
| 2010/0094387 A1 | 4/2010 | Pianca et al. |
| 2010/0268298 A1 | 10/2010 | Moffitt et al. |
| 2010/0269339 A1 | 10/2010 | Dye et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0197602 A1 | 8/2013 | Pianca et al. |
| 2013/0261684 A1 | 10/2013 | Howard |
| 2013/0274844 A1 | 10/2013 | Leven et al. |

FOREIGN PATENT DOCUMENTS

| | | |
|---|---|---|
| EP | 1062973 A1 | 12/2000 |
| EP | 1181947 A2 | 2/2002 |
| EP | 0832667 B1 | 2/2004 |
| EP | 1625875 A1 | 2/2006 |
| EP | 2092952 A1 | 8/2009 |
| WO | 9305844 A1 | 4/1993 |

(56) References Cited

FOREIGN PATENT DOCUMENTS

| | | |
|---|---|---|
| WO | 9308871 A1 | 5/1993 |
| WO | 9732628 A1 | 9/1997 |
| WO | 9916503 | 4/1999 |
| WO | 9916503 A1 | 4/1999 |
| WO | 9936122 A1 | 7/1999 |
| WO | 9955411 A2 | 11/1999 |
| WO | 0038574 A1 | 7/2000 |
| WO | 02/068042 A1 | 9/2002 |
| WO | 02068050 A1 | 9/2002 |
| WO | 03035173 A1 | 5/2003 |
| WO | 03059439 A2 | 7/2003 |
| WO | 03/075414 A1 | 9/2003 |
| WO | 2004030758 A1 | 4/2004 |
| WO | WO 2004/026161 A2 | 4/2004 |
| WO | 2004045707 A1 | 6/2004 |
| WO | 2004047910 A2 | 6/2004 |
| WO | 2004060484 A2 | 7/2004 |
| WO | WO 2004/026161 A3 | 8/2004 |
| WO | 2004112899 A2 | 12/2004 |
| WO | 2005009534 A1 | 2/2005 |
| WO | 2005016451 A1 | 2/2005 |
| WO | 2005023364 A1 | 3/2005 |
| WO | 2005025009 A1 | 3/2005 |
| WO | 2007089974 A2 | 8/2007 |
| WO | 2008053789 A1 | 5/2008 |
| WO | 2008070836 A1 | 6/2008 |
| WO | 2008088565 A1 | 7/2008 |
| WO | 2008088566 A1 | 7/2008 |
| WO | 2008088567 A1 | 7/2008 |
| WO | 2008088568 A1 | 7/2008 |
| WO | 2008130819 A2 | 10/2008 |
| WO | 2009025816 A1 | 2/2009 |
| WO | 2009045772 A1 | 4/2009 |
| WO | 2009045809 A2 | 4/2009 |
| WO | 2009102536 A1 | 8/2009 |
| WO | 2010055421 A1 | 5/2010 |
| WO | 2010055453 A1 | 5/2010 |
| WO | 2012109338 A2 | 8/2012 |

OTHER PUBLICATIONS

Baldi et al.,"A Hydrogel-Actuated Environmentally Sensitive Microvalve for Active Flow Control," Journal of Microelectromechanical Systems, 12(5):613-621, 2003.

Bashir et al., "Micromechanical Cantilever as an Ultrasensitive pH Microsensor,"Applied Physics Letters, 81(16):3091-3093, 2002.

International search report and written opinion dated Aug. 25, 2008 for PCT/US2007/074876.

Krsko et al, "Biointeractive Hydrogels," Materials Today, 8(12):36-44, Dec. 2005.

Seigel, "Hard/Soft Microfabrication for Biosensing and Drug Delivery," University of Minnesota Nanotechnology Presentation, 9 pages total. Downloaded from Internet: <<http://www.business.umn.edu/documents/RonSiegel.pdf.

Steege et al., "Assessment of a New Prototype Hydrogel CO2 Sensor; Comparison with Air Tonometry," The Journal of Clinical Monitoring and Computing 21(2):83-90, 2007.

U.S. Appl. No. 12/177,823, filed Jul. 22, 2008.

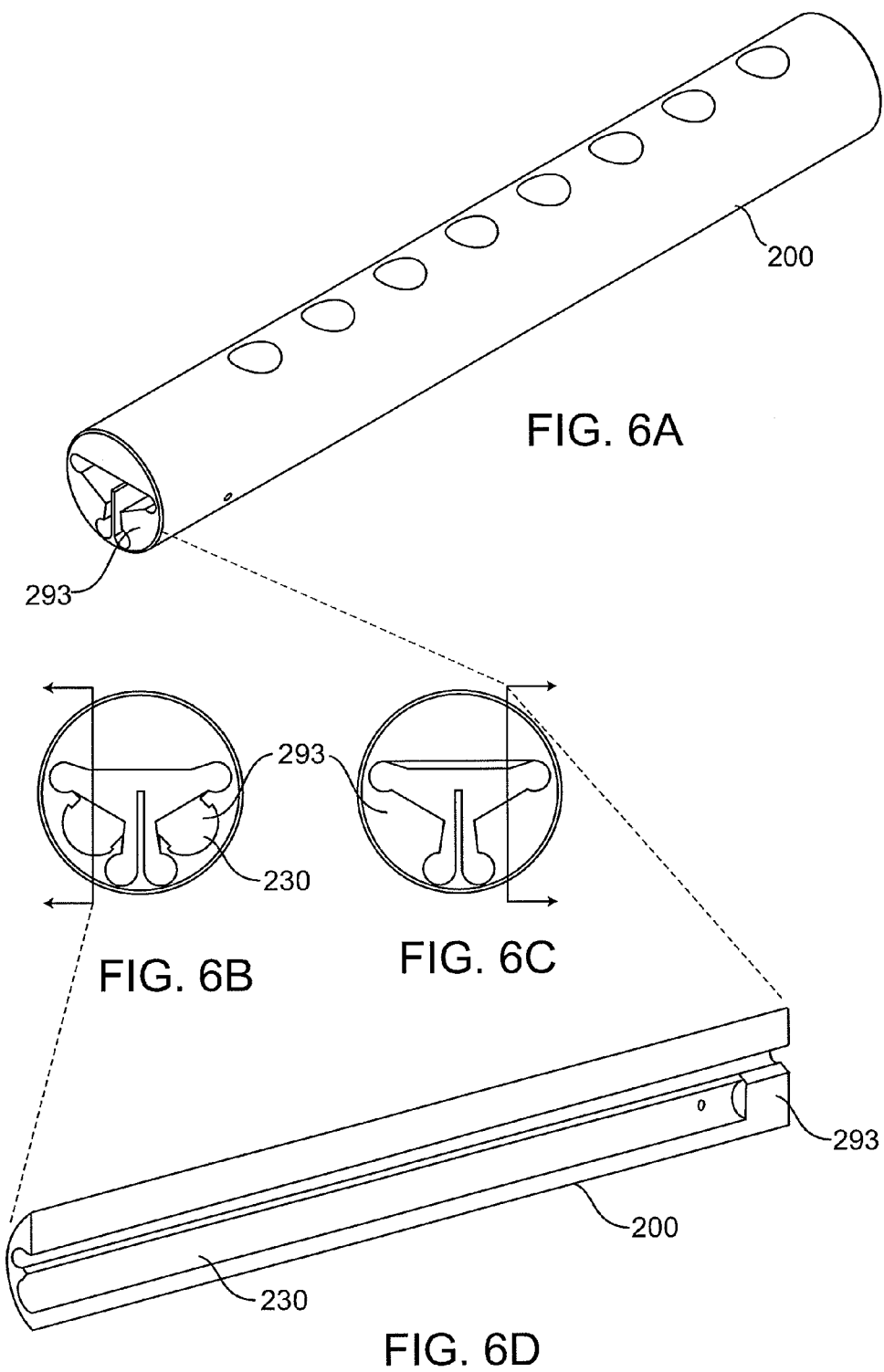

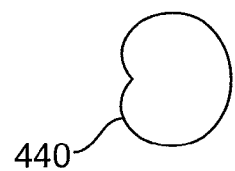
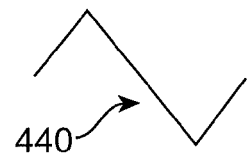
FIG. 13A  FIG. 13B
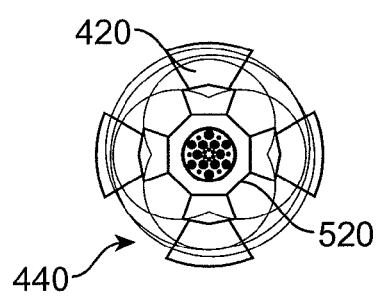
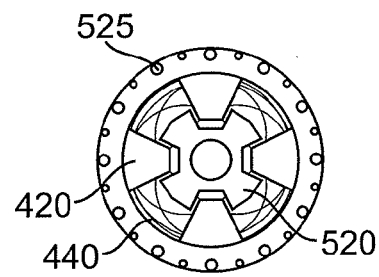
FIG. 14  FIG. 15
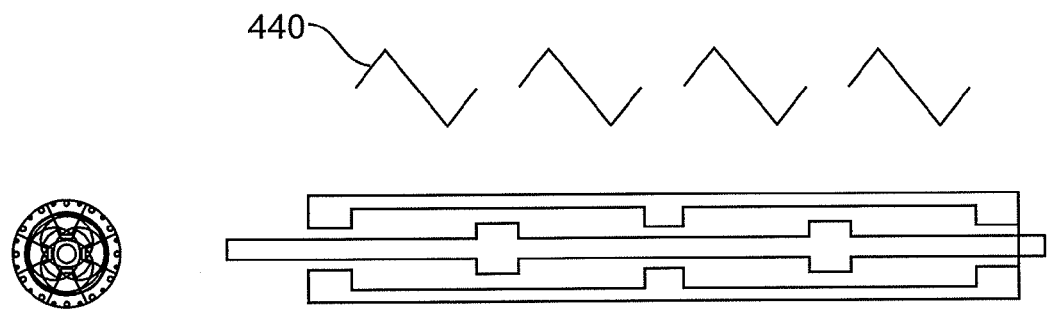
FIG. 16A  FIG. 16B

MULTI-CHANNEL CONNECTOR FOR BRAIN STIMULATION SYSTEM

CROSS-REFERENCES TO RELATED APPLICATIONS

The present application is a continuation of U.S. patent application Ser. No. 12/509,096 now U.S. Pat. No. 7,948,329 filed Jul. 24, 2009, which is a divisional of U.S. patent application Ser. No. 11/830,565 now U.S. Pat. No. 7,583,999, filed Jul. 30, 2007, which claims the benefit of U.S. Provisional Patent Application No. 60/820,914, filed Jul. 31, 2006, the full disclosures of which are incorporated herein by reference.

BACKGROUND OF THE INVENTION

1. Field of the Invention

This invention relates generally to medical apparatus and methods, and more specifically to a connector used to electrically couple a brain stimulating and recording probe or lead to a lead extension, pulse generator or other neurological device.

Implanting medical devices such as probes or leads within the cranium is an increasingly important approach for treatment of diseases such as Parkinson's Disease, essential tremor and dystonia. Implants may be used to treat a wide array of disorders, such as depression, epilepsy, dystonia, obsessive compulsive disorder, obesity, chronic pain as well as in post-stroke rehabilitation. Most of these devices interact with the brain by applying current through an electrode. In addition, infusion of drugs through a chronically implanted probe has been proposed in the medical literature either as a primary treatment, or as an adjunctive treatment to electrical stimulation, in patients with Alzheimer's and Parkinson's Diseases, among others.

Current implantable probes are typically configured as small diameter cylinders or tubes, with several circumferential metal stimulating rings near the distal tip, and an electrically passive central axial lumen. The metal stimulating rings are used to provide electrical stimulation to tissue such as the brain, while the central axial lumen can be used to deliver the probe over a guidewire or stylet during the implantation procedure. Helical wires course through the body of the probe and terminate on another set of metal connector rings which fit into a connector integrated into a lead extension. The conductors are encased in a flexible polymer to provide insulation.

Brain stimulating and recording probes are typically connected to a lead extension through a linear array of cylindrical screw terminals. An electrical connection is made when a screw is rotated so as to impinge upon one of the stiff metal connector rings, and force it against a stranded wire which is continuous with conductors of the lead extension. The screw provides contact pressure, and under this pressure individual wire strands are slightly displaced against the surface of the stiff connector ring, providing the elements of a secure electrical connection. Flexible segments between the stiff connector rings provide mechanical isolation, so that each contact may be formed independently.

Connectors are often cylindrical with a diameter that matches the stimulating probe body and are robust enough to accommodate physical manipulation. Additionally, usually, one screw must be tightened for each electrical connection. The torque applied to the screw must be controlled carefully since over-tightening can result in damage to the screw terminal or probe, and under-tightening can result in a poor connection.

Current probe or lead designs steer electrical current into tissue by shaping the electrical field through coordinated stimulation of multiple contact sites, such as those disclosed in U.S. patent application Ser. No. 11/828,547 filed Jul. 26, 2007, the entire contents of which are incorporated herein by reference. Such probes may also record neuronal activity near stimulation sites to evaluate the state of the brain and/or disease process to evaluate the local neuronal effects of shaped electrical stimulation. Thus, more electrical contact sites are needed to integrate stimulating and recording functions, and construction of a high density multi-channel electrical connector is necessary to couple the stimulating probe with a pulse generator and controller.

For these reasons as well as others, it would be desirable to provide high density multi-channel electrical connectors for brain stimulation systems that are sterilizable, implantable and easy to use in a surgical environment. It would be particularly desirable to provide connectors which are the same diameter or smaller than the stimulating probe body. Providing small size, low profile connectors allow them to be easily implanted subcutaneously using existing surgical instruments such as guide tubes and tunnelers. It is also desirable to provide a symmetrically shaped connector so that the lead extension does not move excessively or apply excessive torque after implantation.

2. Description of Background Art.

Prior patents and publications describing lead connectors include: U.S. Publication Nos. 2004/0039434 and U.S. Pat. Nos. 4,236,525; 4,437,474; 4,603,696; 6,980,863; and 6,912,423.

BRIEF SUMMARY OF THE INVENTION

The invention generally provides a connector for electrically connecting a plurality of electrical conductors. The connector is optimized to connect a neurological device such as a brain stimulating and recording lead to a lead extension or a stimulation and/or controller unit. The connector is small and suitable for implantation into the body. Its shape and configuration facilitates convenient handling by surgeons and other healthcare professionals in the operating room. Its size minimizes the metal required to make electrical connections, which in turn improves compatibility with imaging systems which depend on magnetic fields, such as magnetic resonance imaging (MRI), spectroscopy, and magneto encephalography (MEG).

In a first aspect of the present invention, a connector for coupling a neurological device with a lead extension comprises a male connector having a plurality of electrical contacts axially arranged along the connector and electrically insulated from each other. The connector also includes a female connector having one or more channels axially disposed therein and a plurality of conductors axially arranged thereon. The plurality of conductors are electrically insulated from each other. Also, at least one indexing element is disposed adjacent to one or more of the channels and the indexing element allows the male connector to be received into the one or more channels in a defined orientation relative to the channel, thereby forming at least two electrical connections along two or more axial positions.

In a second aspect of the present invention, a connector system comprises a connector comprising a male connector, a female connector, and one or more channels axially disposed in the female connector, wherein at least one of the channels has an indexing element adapted to receive the male connector in a defined orientation relative to the female connector, thereby forming at least two electrical connections along two or more axial positions. The system also includes a neurological device that is electrically coupled with at least one of the male and female connectors and a lead extension also electrically coupled with at least one of the male and female connectors. An implantable and controllable pulse generator is also included in the system. The pulse generator is adapted to provide an electrical stimulus to the neurological device via the male and female connectors. The system may include a protective sheath that is adapted to cover the male and female connectors as well as an anchoring device. The anchoring device is adapted to removably fix the neurological device to a patient's head. Sometimes the system may include a patient programmer that is adapted to control the pulse generator.

In a third aspect of the present invention, a method for connecting a neurological device with a lead extension comprises positioning a male connector relative to a female connector having one or more channels disposed therein and inserting the male connector into one of the channels thereby forming at least two electrical connections along two or more axial positions. The male and female connectors are releasably fastened together and then the coupled male and female connectors are implanted into a patient. The step of fastening may comprise tightening a screw and also the step may comprise rotating the male connector relative to the female connector thereby forming a secure electrical connection therebetween.

The male connector may be electrically coupled with a neurological device such as a brain stimulating and recording lead. The female connector may be electrically coupled with a lead extension or other medical device. Sometimes the female connector and the lead extension are fixedly coupled together or they may be integral with one another. Sometimes at least some of the conductors of the female connector are integral with wires in the lead extension. Often, the male and female connectors are compatible with magnetic resonance imaging. Also, when the male and female connectors are engaged together they may form a hermetic seal or be wrapped by a sheath which forms the seal. The sheath usually covers at least a portion of the male and female connectors.

Sometimes the male connector comprises two or more elongated members. At least one of these elongated members may be hemi-cylindrically shaped or the male connector may have a cross-sectional shape selected from the group consisting of rectangular, triangular, elliptical, circular, square and ovoid. Often the female connector has a longitudinal axis and the at least two electrical connections are symmetrical thereabout. The female connector may slidably receive the male connector.

Sometimes the male connector may comprise a rod receivable by the channel and wherein the plurality of electrical contacts are disposed on tabs radially extending outward from the rod, thus the male connector rotationally engages the female connector. Two or more tabs may be disposed circumferentially around the rod at two or more axial positions, with each tab having at least two electrical contacts. Sometimes, the rod comprises a central cavity through which electrical conductors from the neurological device traverse at least partially and the electrical conductors may terminate at electrical contacts disposed on the tabs. The tabs may be spaced apart by valleys through which electrical conductors from the neurological device traverse. Sometimes the conductors comprise spring terminals and the spring terminals may follow a substantially helical path along a longitudinal axis of the female connector, forming a cardiod shape when viewed from an end of the female connector.

The connector may also comprise a fastener adapted to releasably compress at least two of the conductors in the female connector against at least two of the contacts in the male connector thereby forming at least two secure electrical connections therebetween. Sometimes the fastener comprises a screw that is threadably engaged with the female connector. Sometimes the connector may comprise a rotating camshaft or a plug slidably received by the female connector. The camshaft or plug is adapted to releasably compress at least two of the conductors in the female connector against at least two of the contacts in the male connector thereby forming at least two secure electrical connections therebetween.

The male connector may engage the female connector forming a body with a profile that is substantially cylindrical such that when the body is rotated it has substantially the same profile in any position. The male connector may comprise a polymer selected from the group consisting of polyetheretherketone (PEEK), polyetherimide (Ultem™) and polyimide. Also, the indexing element may be integral with the female connector and it may be a pin. Sometimes the connector may have a central lumen that is adapted to accommodate a guidewire, stylet or fluid. The female connector may be of monolithic construction and it may comprise a polymer selected from the group consisting of polyetheretherketone, polyetherimide and polyimide. The female connector may also be fabricated substantially from a metal such as stainless steel. Sometimes the female connector comprises a dividing element separating two axial groups of conductors with the plurality of contacts and disposed in the dividing element.

The plurality of conductors may comprise a conductor selected from the group consisting of thin film conductors, thick film conductors, wire conductors and printed circuit conductors. The connector may also comprise a cassette, wherein the male connector is received in the cassette and the cassette is received in the female connector. Also included is a cassette fastener which is adapted to releasably couple the cassette, the male connector and the female connector together. The cassette fastener may threadably couple the cassette, the male connector and the female connector together. The connector may also comprise a bump stop which is adapted to help align the male connector with the female connector and also to prevent the male connector from moving in at least one direction relative to the female connector. The connector also may include a protective sheath adapted to cover the male and female connectors.

These and other embodiments are described in further details in the following description related to the appended drawing figures.

BRIEF DESCRIPTION OF THE DRAWINGS

FIG. 6A shows a perspective view of an exemplary embodiment of a connector.

FIG. 6B shows a front end view of the connector in FIG. 6A.

FIG. 6C shows a back end view of the connector in FIG. 6A.

FIG. 6D shows a longitudinal cross section of the connector in FIG. 6A.

FIGS. 13A-13B illustrate the shape of helical cardioid spring contacts.

FIGS. 14 and 15 illustrate how connecting tabs engage cardioid spring contacts.

FIGS. 16A-16B illustrate the multi-channel connector of FIG. 10 assembled.

DETAILED DESCRIPTION OF THE INVENTION

Figure 1:
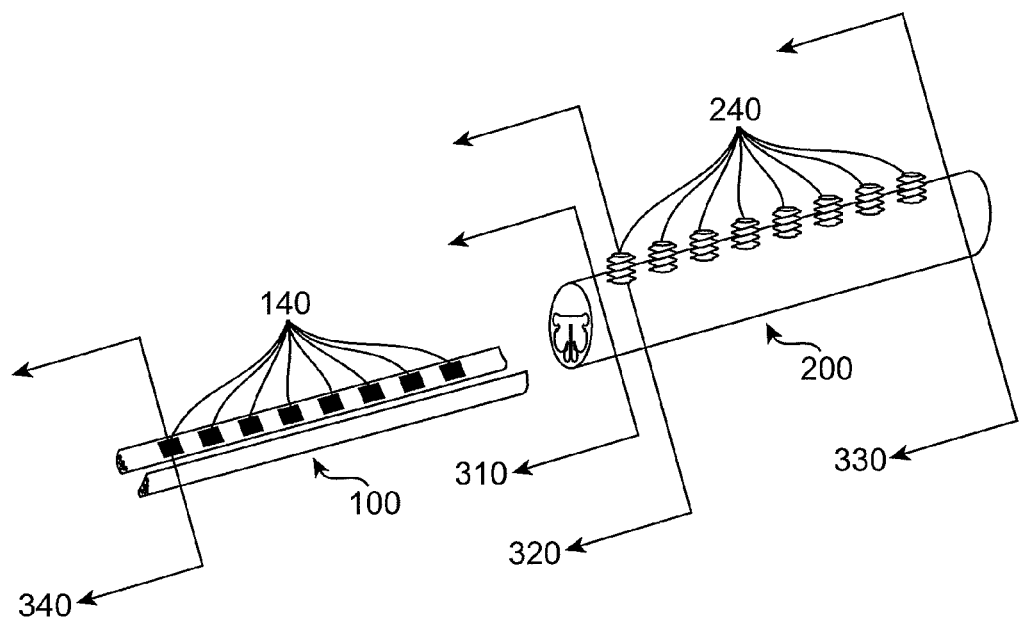
FIG. 1 shows an embodiment of a multi-channel connector.

FIG. 1 illustrates a preferred embodiment of the present invention. A multiple contact connecting terminal, also referred to as a male connector 100 is integrated with a brain stimulating and recording probe. It is comprised of two hemi-cylindrical contact strips, each with a linear array of electrical contacts 140. The hemi-cylindrical strips 100 insert into a cylindrical multiple contact connecting terminal also referred to as a female connector 200 integrated with a lead extension. Screws 240 provide pressure to ensure secure electrical connections.

Figure 2:
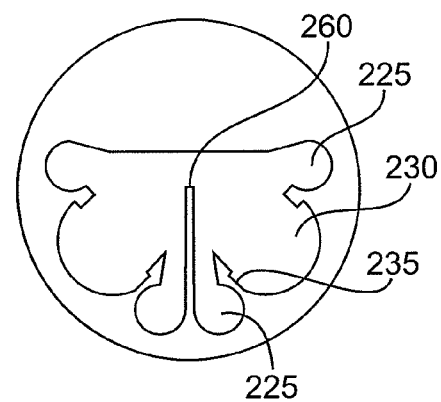
FIG. 2 illustrates a cross-section of the embodiment shown in FIG. 1.
Figure 8:
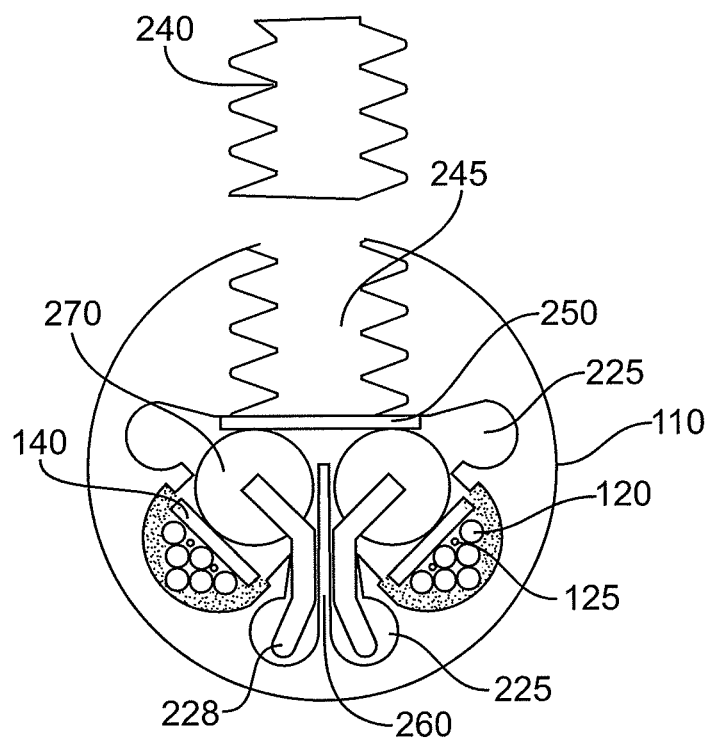
FIG. 8 illustrates a cross-section of an assembled multi-channel connector.

FIG. 2 illustrates a cross-section at position 310 of the embodiment illustrated in FIG. 1. This part could be manufactured by extrusion, or it could be machined. The probe terminal strips 100 slide into cavities or channels 230, and are indexed by the flat surface 235. In alternative embodiments the space 235 could be a hemi-cylinder, and a small wire, rod or flat insert could index the terminal strips 100 to ensure that each strip can be inserted into one cavity. Such inserts need not course the entire length of the connecting terminal 200, but could course only a limited axial distance in the vicinity of cross section 330. It could also have a taper at its distal end, to facilitate insertion and proper seating of the terminal strips 100, in the manner of a chamfer. The dividing wall 260 separates and electrically insulates compressible contacts 270 (FIG. 8). It may be an integrated feature of the lead extension terminal 100, or it may be a separate part. Lead extension wires course through the cavities 225 at more proximal stations.

Figure 3:
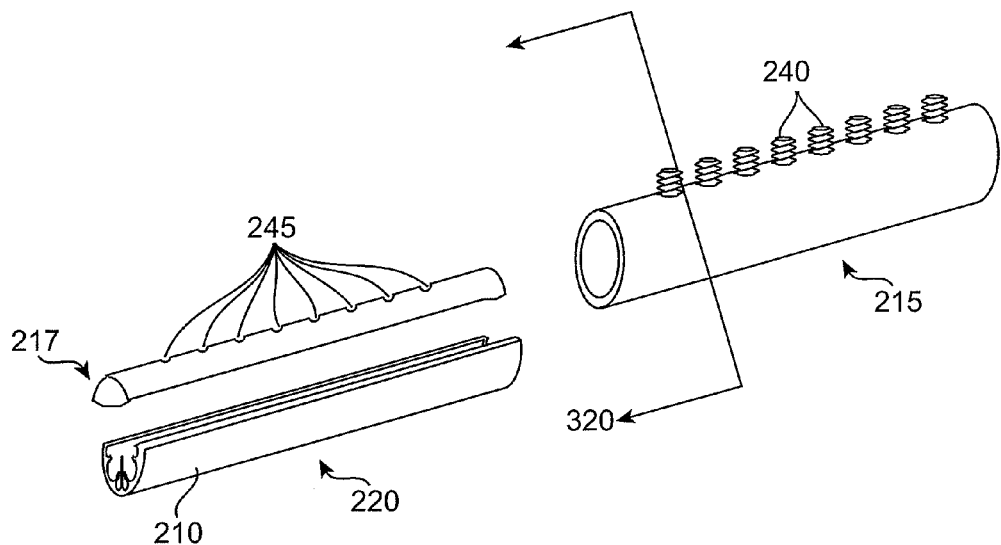
FIG. 3 illustrates another embodiment of a multi-channel connector.

FIG. 3 illustrates an alternative embodiment of the lead extension terminal, in which a positioning cassette 220 inserts into the cylindrical terminal body 215. This embodiment facilitates fabrication by machining A spacer 217 positions the cassette 210 properly within the cylinder. Holes 245 permit screws 240 to travel through the spacer 217 to press upon the internal parts and effect a secure electrical connection. The body 215 is a cylinder. During manufacturing, the spacer 217 and cassette 220 may be inserted into the body 215 before drilling and tapping the holes 245, at which time the spacer 217 may be permanently attached to the body 215 by an adhesive. The cylindrical terminal body 215 may be made of an engineered plastic, or for extra strength may be made of a metal such as stainless steel, MP35N or other cobalt-chrome alloy, or tungsten. In one particular embodiment, the cylindrical terminal body is a 6 or 7 gauge thin-walled stainless steel hypodermic tube.

Figure 4:
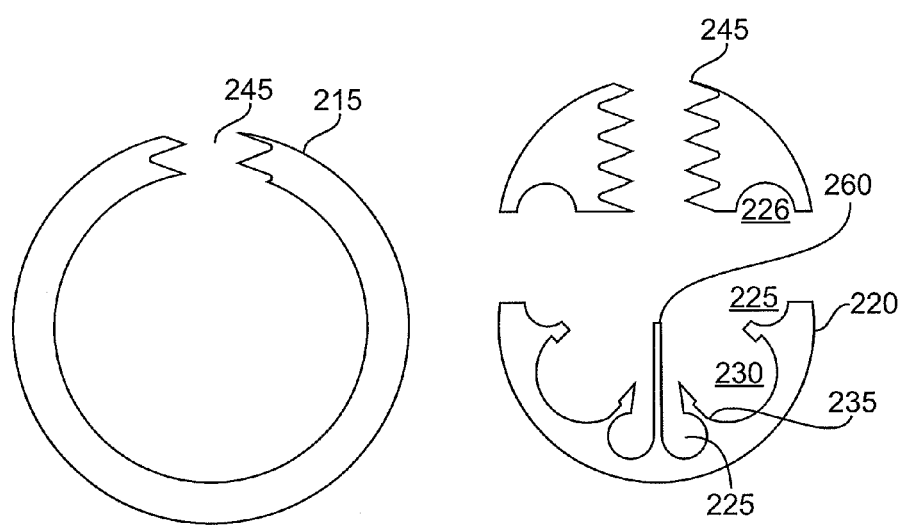
FIG. 4 illustrates a cross-section of the embodiment shown in FIG. 3.

FIG. 4 provides an enlarged cross-sectional view of each of the major components of the embodiment in FIG. 3. The probe terminal strips 100 slide into the cavities 230, indexed by a flat surface 235. As in the embodiment of FIG. 2, in variations of this embodiment space 235 could be a hemi-cylinder, and a small wire, rod or flat insert could index the terminal strips 100 to ensure that each strip can be inserted into one cavity. Such inserts need not course the entire length of the connecting terminal 220, but could course only a limited axial distance in the vicinity of cross section 330. It could also have a taper at its distal end, to facilitate insertion and proper seating of the terminal strips 100, in the manner of a chamfer. Wires integrated with the lead extension course through the spaces 225 and 226. In this embodiment the spaces 226 in the spacer 217 may be machined by a larger tool than the spaces 225, to facilitate insertion of the assembled cassette into the connector body 215 with the lid of the cassette 217 pre-attached. Holes 245 are adapted to receive screws 240.

Figure 5:
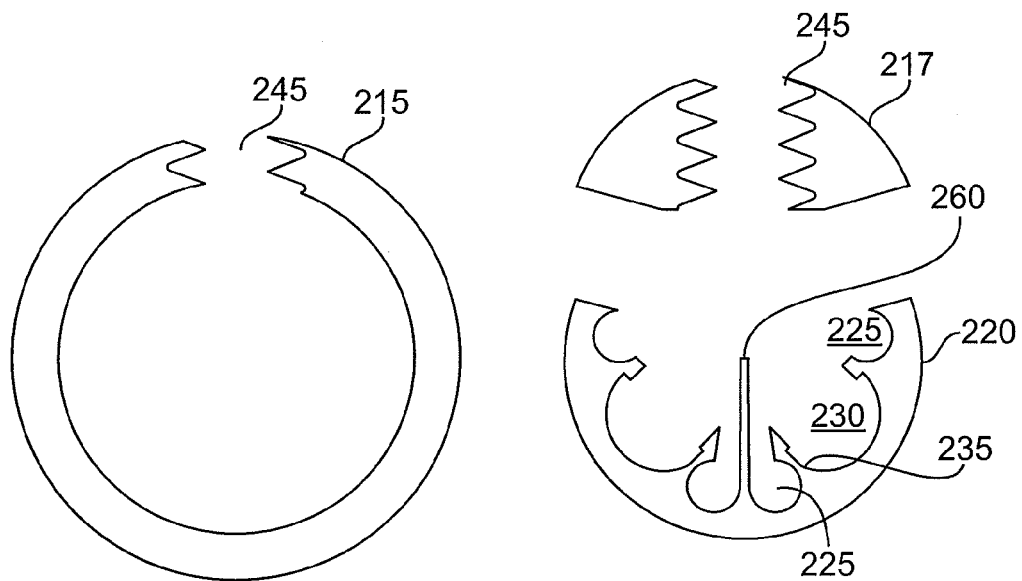
FIG. 5 illustrates still another embodiment of a multi-channel connector.

FIG. 5 illustrates an alternative cassette based embodiment, where the spaces 225 for the lead extension wires lay entirely within the cassette 220. FIGS. 4-5 illustrate how different embodiments of the invention can present different manufacturing challenges. For example, if the embodiment of FIG. 4 is machined, the lower surface can be fabricated by a single flat cut, followed by machining two channels 226. The embodiment of FIG. 5, on the other hand, requires three precise flat cuts.

Figure 6:
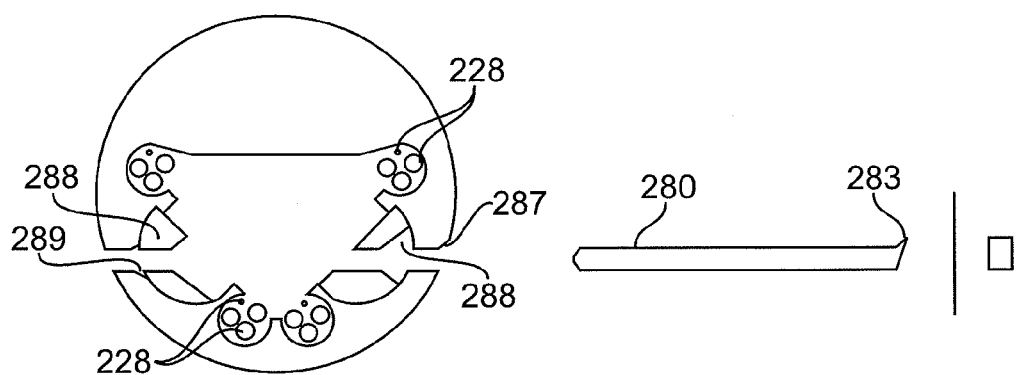
FIG. 6 illustrates the use of an alignment pin for proper indexing of connector components.

FIG. 6 illustrates the position of an alignment pin in the embodiments of FIGS. 1 and 3, at section 330. The terminal strips 100 are first positioned into nearly correct alignment by pushing against the end of the lead extension terminal body 210 or 215. Then a single pin 280 is inserted through the lead extension terminal body and the two terminal strips. The pin 280 may be angled or chamfered to facilitate insertion, and the receiving surfaces 287, 288, 289 are also chamfered or beveled to facilitate final alignment by the pin. In alternative embodiments the receiving surfaces need not be beveled. The stop flare 283 may fit flush against the receiving surface 287, and may be shaped by forging.

FIGS. 6A-6D illustrate an embodiment which incorporates a bump-stop 293, a mechanical feature which facilitates course alignment of the contact strips with contact pads, to facilitate insertion of the pin 280. The pin 280 ensures fine alignment. FIG. 6A shows a perspective view of the connector, with the back end, showing the bump-stop 293 in the foreground. FIG. 6B shows an end view of the front of the connector, with receiving cavities or channels 230 terminated with the bump-stop 293. FIG. 6C shows an end view of the back of the connector, with the bump-stop 293 obscuring the view of the receiving cavities or channels 230. FIG. 6D shows a cross-section view showing the receiving cavity or channel 230 terminated by the bump-stop 293.

Figure 7:
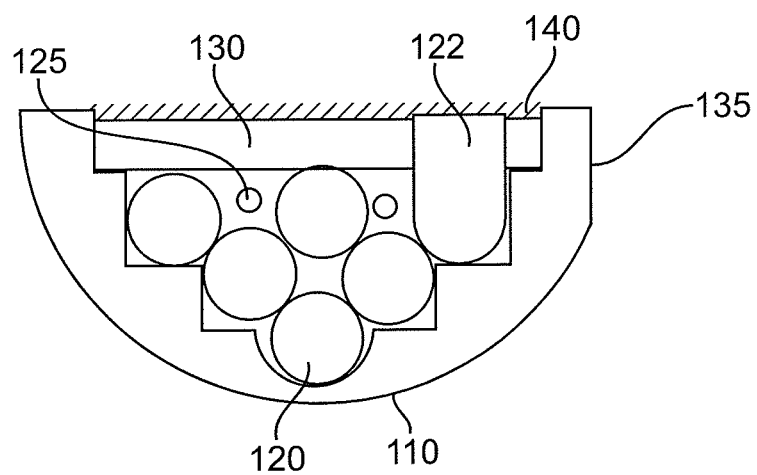
FIG. 7 illustrates a cross-section of the multi-contact terminal portion of the embodiment shown in FIG. 1.
Figure 18A:
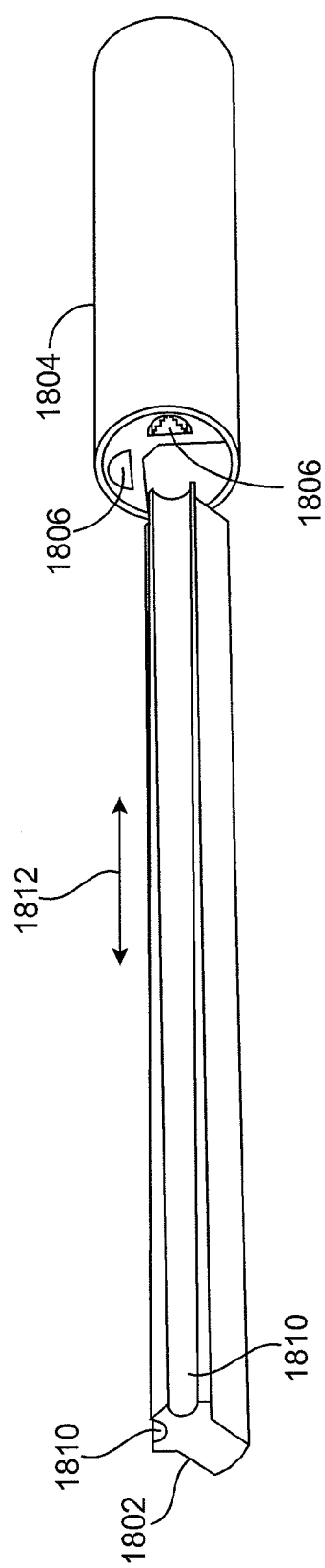
FIGS. 18A-18B illustrate the use of plug to form electrical contacts between the male and female connectors.
Figure 18B:
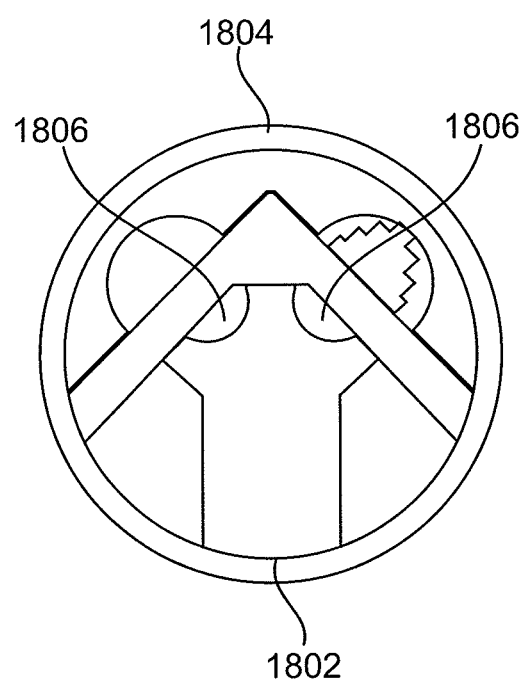

FIG. 7 illustrates a cross-section of the probe terminal 100 in the embodiment of FIGS. 1 and 3, including the conductors 120, 125, and the terminal strip 130. The terminal strip provides a firm surface to support the electrical contact 140 as the compressible contact 270 (FIG. 8) is forced against it by the screw 240 and pressure plate 250. At each electrical contact, one conductor from the probe penetrates the terminal strip 130 to make a connection with the electrical contact. For example, stimulating conductor 120 contacts with electrical contact 140 at position 122. The connection can be made by welding, or by thin film metallization. The profile of the terminal shell 110 can be thicker in later cross-sections, as wires terminate. In alternative embodiments, the key surface 135 may only be at the end of the probe terminal, beyond the alignment pin. In alternative embodiments, a divot in the terminal strip 130 accommodates a guidewire when two terminal strips appose each other. In other embodiments, the flat surface 135 may extend for the length of the terminal 100, and a guidewire may course alongside the apposed strips, and be channeled to the center of the stimulating and recording probe past the point where electrical connections are made. In some alternative embodiments, the pressure plate 250 can be forced against the compressible contacts 270 by a plug as illustrated in FIGS. 18A-18B. FIG. 18A shows a perspective view of plug 1802 which is slidably received axially in the direction of arrow 1812 into female 25 connector 1804 having channels 1806 which receive the male connector. Plug 1802 also has channels 1810 which provide space for conductor wires. FIG. 18B shows a side view of FIG. 18A. In still other embodiments, a rotating camshaft may be used instead of the plug.

In alternative embodiments, the connecting terminal integrated with the brain stimulating and recording probe could be constructed with printed circuit or flexible circuit technology. For example, two planar multilayer printed circuits could be apposed to each other, and ground or machined into a cylinder of the appropriate diameter so that the contact an fit inside of a stylet when integrated with a medical lead. In alternative embodiments, the shape need not be a hemi-cylinder, and may be flat, rectangular, triangular, elliptical, circular, square or ovoid in cross-section, although such embodiments may be incompatible with existing surgical instruments such as a probe insertion guide tube.

FIG. 8 illustrates a cross-section through the assembled connector. Each screw secures two electrical connections. Engineered plastics such as PEEK, Ultem and/or Kapton ensure high strength and close tolerances between the parts. The compressible contacts 270 accommodate variations in the precise distances between parts, as well as insuring that microscopic displacement can occur between conductors in contact with each other. When the screw 240 impinges upon the pressure plate, compressible contacts 270 are forced against the electrical contacts 140. As the contacts compress, at the micro level, the conductive surfaces are displaced against each other and plastically deformed, ensuring a secure electrical connection. In different embodiments of the invention, the compressible contacts could be a modified twist pin, a fuzz button, a short rod, tube, or block of conductive elastomer, or other compressible conductor known to those skilled in the art. The orientation of the flat electrical contacts 140 is approximately 45° relative to the direction of the force generated by the screw 240, to ensure stable positioning of the compressible contacts 270. A barrier wall 260 insulates the compressible contacts from each other, and is of a height which provides electrical insulation, while not interfering with the downward displacement of the pressure plate 250. At each screw position, each of two lead extension wires is integrated into a compressible contact.

In alternative embodiments, the dividing wall could be a thin multilayer circuit board, circuit card or flexible circuit, with conducting pads along the upper most portion, and conductors along the lower portion and within the inner layers. In such embodiments, the upper cavities for lead extension wires 225 would not be needed, and the lower cavities for lead extension wires could assume the form of a slot positioning the dividing wall 260.

Figure 9:
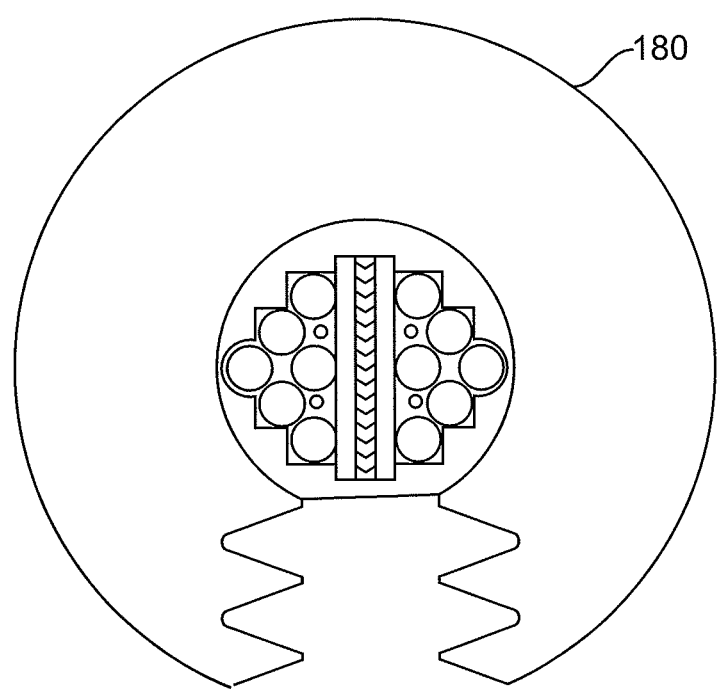
FIG. 9 illustrates a protective sheath used for handling the multi-contact terminal.

FIG. 9 illustrates a protective cover 180 for easy handling of the multiple contact connecting terminal integrated with the brain stimulating and recording probe 100. It is a cylinder, with a central cavity sized to receive the two branches of the connecting terminal apposed to each other. In the embodiment illustrated, a single set screw captures the terminal inside the cylinder. In an alternative embodiment, a pin similar to that illustrated in FIG. 6, but with a head that facilitates quick and easy removal. Such a pin could take the form of a loop of fine wire, such as a fine wire suture, which could be twisted to temporarily capture the terminal within the cover. In an alternative embodiment, the protective cover may be a thin elastomeric sheet.

Figure 10:
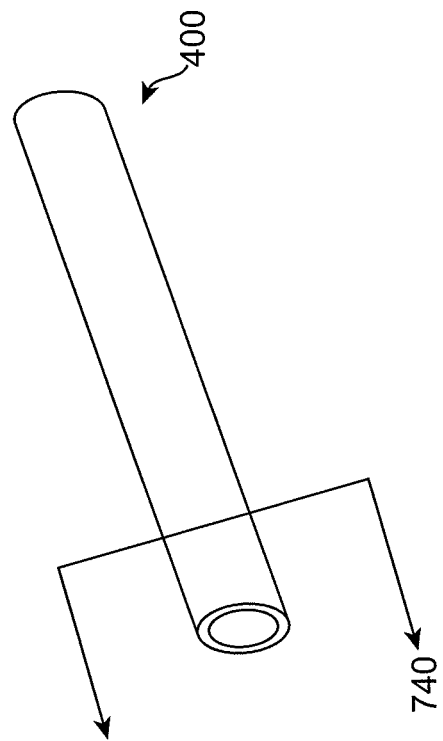
FIG. 10 illustrates another embodiment of a multi-channel connector.
Figure 10:
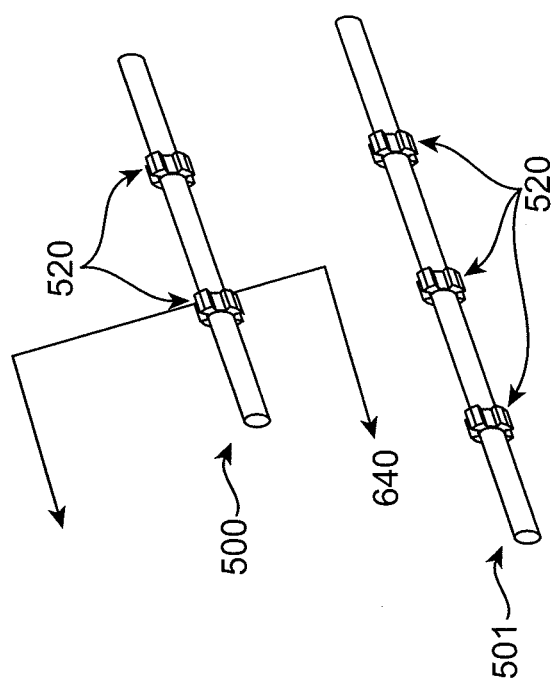

FIG. 10 illustrates an alternative embodiment of the invention, in which connecting contacts are made by a twist action. A multiple contacting connecting terminal 500 at the end of the brain stimulating and recording probe inserts into a multiple contact connecting terminal at the end of the lead extension. Up to 8 electrical contacts appear on projecting surfaces of each multi-contact tab 520. An electrical connection is made when the probe terminal 500 is twisted, wiping electrical contacts on the tabs 520 against helical spring contacts within the body of the lead extension terminal 400. Connecting terminal 500 has two contact tabs 520 while connecting terminal 501 has three contact tabs 520.

Figure 11B:
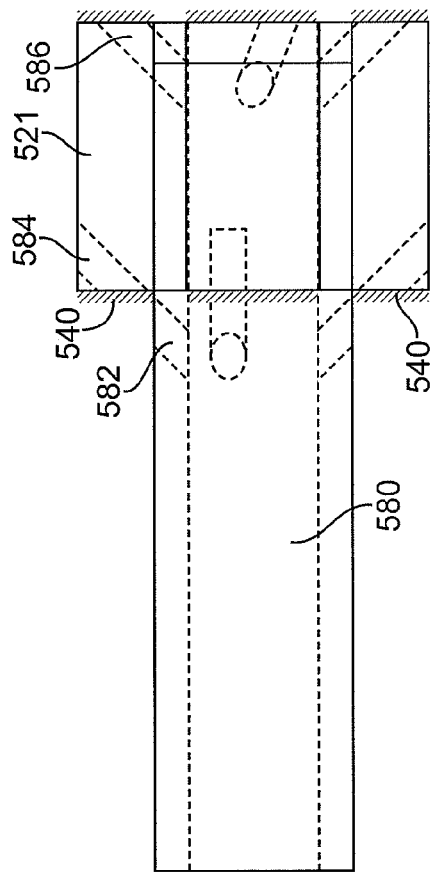
FIGS. 11A-11B illustrate the connecting tabs in the embodiment of FIG. 10.
Figure 11A:
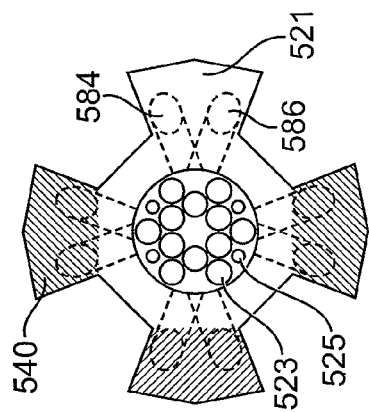

FIGS. 11A-11B illustrate an embodiment of the connecting tabs 520 of the connector embodiment of FIG. 10. FIG. 11A highlights tabs 521 and FIG. 11B is a side view of the connector. Four tabs 521 extend from the shaft. Two electrical contacts 540 appear on each tab, one facing towards the opening of the lead extension terminal 400, and one facing away from the opening. In the axial view, the electrical contact 540 is omitted from one tab for clarity. Likewise for clarity, the back tab is omitted from the parasagittal view. Stimulating 523 and recording 525 wires course through a central cavity 580 and exit to achieve continuity with the electrical contacts 540. The vias 582, 586 are angled in the same direction, to facilitate fabrication of the probe terminal as a monolithic part, with the conductors threaded into the terminal. Other embodiments may include a cavity 590 to accommodate a guidewire, as seen in FIG. 12.

Those skilled in the art will recognize that such a shape can be constructed through machining, which will generate an extra hole 584, as a byproduct of the fabrication process. One way to machine such a part is to use a lathe to bore the central cavity 580 in a rod. Next, grooves are machined into the rod at the points where the multi-tab terminals 520 will be placed, with the deepest part of the grove at the outer extent of the tabs, and the sides of the groove orthogonal to the axis of the vias 582. Additional grooves are machined with sides orthogonal to the vias 586. A drill is used to form the holes which become the vias 582 and the accessory holes 584, as well as the holes which become the other vias 586. On the lathe, the material between the tab faces and beyond the extent of the tabs is removed.

Figure 12:
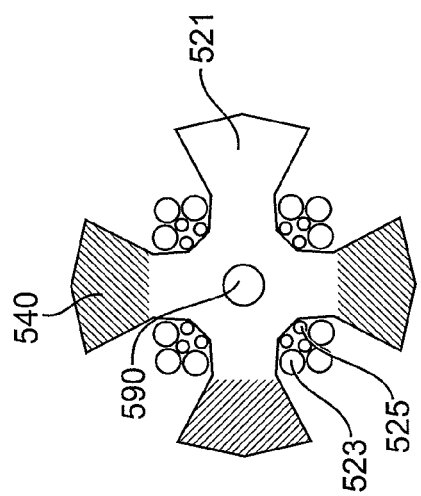
FIG. 12 illustrates another embodiment of the connecting tabs in the embodiment of FIG. 10.

FIG. 12 illustrates an alternative embodiment of the multiple tab terminals 521, in which the probe conductors course outside of the terminal body. This embodiment has the advantage of simpler fabrication compared to the embodiment in FIGS. 11A-11B. It has the disadvantage of being weaker compared to the embodiment of FIG. 11, because the material forming the shaft of the terminal is placed closer to the center of the shaft. A central cavity 590 can accommodate a guidewire or fluid. Again, the electrical contact 540 has been omitted from one of the tabs 521 so that the tab may be clearly labeled.

FIG. 13A illustrates the basic shape of the helical cardioid spring contacts 440 of the extension lead terminal. Electrical contact is made when the probe terminal shaft is rotated, so that the flat electrical contacts 540 are wiped against these spring contacts. These contacts may be constructed of a conventional material. An example of a conventional material is an alloy of beryllium and copper, with the possible addition of nickel and cobalt. They may also be made of a biocompatible material, and may be gold plated.

FIGS. 14 and 15 illustrate some of the special advantages of such a shape. Four such springs are oriented along equally spaced angular directions, and press against each face of each multiple contact tab 520. The ends of the spring are closer to the center of the connector. One end is fixed in a support tab 420, and the other scrapes against the contact 540. FIG. 13B illustrates the configuration in which the contacts are engaged. FIG. 14 illustrates the configuration in which the contacts are not engaged, and the individual tabs probe contact tabs 521 can slide through the spaces between the springs as the probe terminal is inserted into the lead extension terminal. FIGS. 16A-16B show an end view and side view of the components of the multi-channel connector FIG. 10 assembled.

Figure 17:
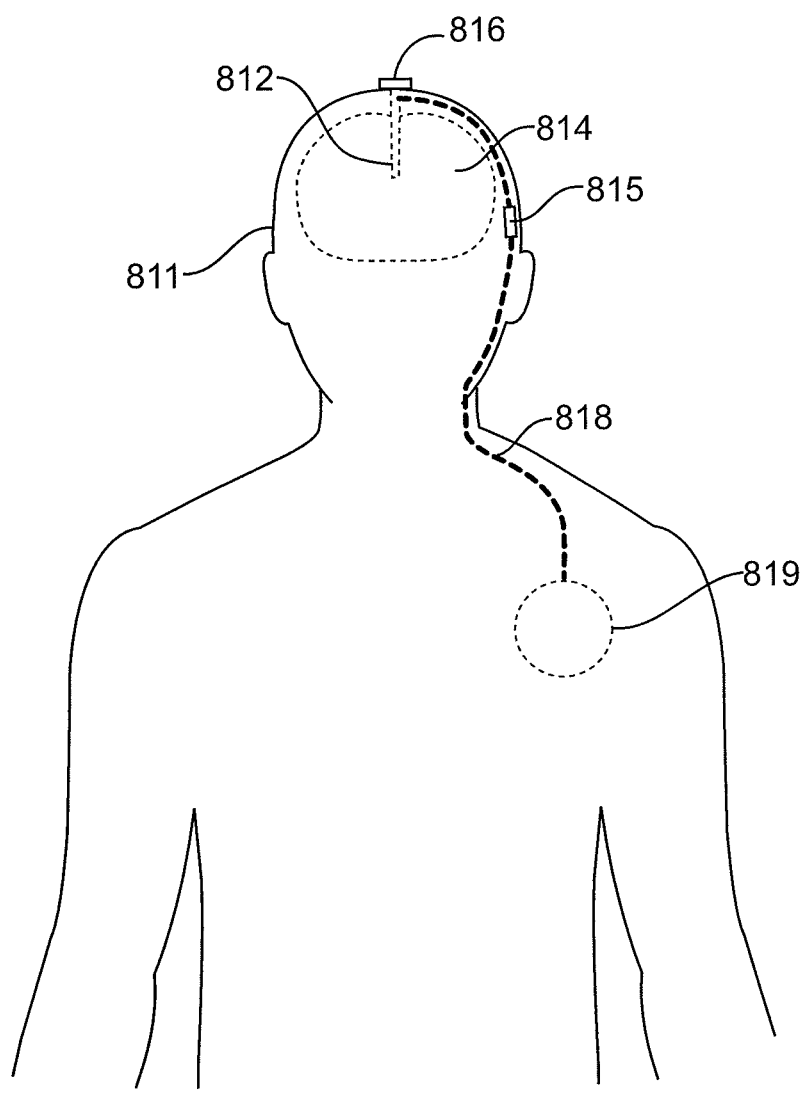
FIG. 17 shows a brain stimulating and recording lead implanted in a patient.

FIG. 17 shows a monitoring and modulating probe or lead 812 secured to the skull 811 of a patient with a fixture 816 and implanted into brain tissue 814. An extension lead 818 couples the probe 812 with a controllable pulse generator 819 via connector 815. Connector 815 comprises a male and female connector coupled together. The lead often runs under the patient's skin, although it may not and the controllable pulse generator 819 may be implanted or it may remain external to the body of the patient. Additional details on a fixture for securing the probe to the skull are disclosed in U.S. Provisional Patent Application No. 60/908,367 filed Mar. 27,2007, the entire contents of which are incorporated herein by reference.

Stimulating Leads.

Probes often have annular electrodes on their distal ends. An electrode divided into two stimulation sites is capable of orienting a dipole along one axis. When the annular electrode is divided into three stimulation sites, a dipole may be generated along any direction in a plane. Three stimulation sites per annular electrode is therefore advantageous as being the minimum number of stimulation sites per electrode required to orient a dipole along any direction in a plane. Using the minimum number of stimulation sites is also advantageous because it minimizes the number of conductors which must pass through the probe and permits maximum current density through any recording site to modulate the brain tissue.

Figure 32:
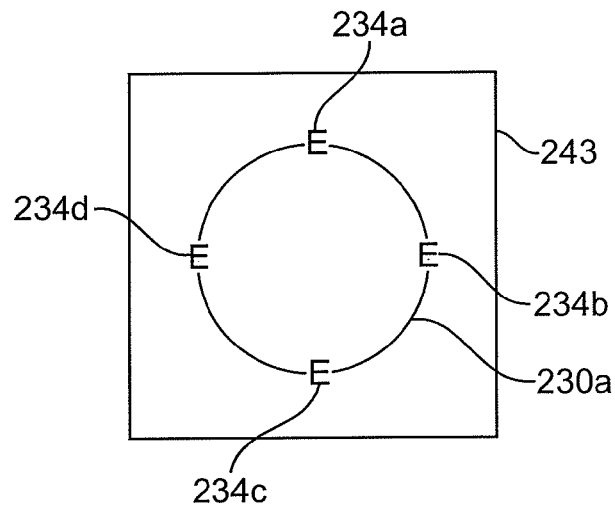
FIG. 32 illustrates a model of the magnitude of a dipole generated by four stimulation sites separated by 90°.

When current density is limited by brain tissue tolerance, a broken ring of stimulation sites can deliver a greater stimulus in some directions than others. For example, consider four stimulation sites arranged as a broken ring around a cylindrical probe, with two sites aligned with a transverse axis (X), and the other two sites aligned with an orthogonal transverse axis (Y). This configuration may generate an electrical dipole of any orientation within the plane of the stimulation sites by linear summation of two dipoles resulting from passing electrical current between opposite pairs of stimulating sites. To generate a dipole of magnitude (m) and orientation θ relative to axis (X), a current of magnitude (m/d) cos θ is passed through stimulating sites aligned with (X), and magnitude (m/d) sin θ is passed through the stimulating sites aligned with (Y), and where d is the distance from the origin. As θ changes, the locus of the dipole magnitude traces a circle. It may be desired to limit the current density at any single electrode to be less than some maximum value, so that heat or other undesired side effects of stimulation may be limited. With such a constraint, the maximum dipole that may be generated by a broken ring of four stimulation sites as a function of the angle θ traces a square 243, as seen in FIG. 32. The largest dipole magnitudes are for orientations midway between the axes (X) and (Y), at the corners of the square, because both pairs of stimulation sites carry the maximum permitted current. The smallest dipole magnitudes are for orientations along the axes (X) and (Y), because only one pair of stimulation sites carries non-zero current.

Compare the above scenario to an embodiment with three stimulation sites arranged in a broken ring or annulus about a cylindrical probe. If the axial extent of the electrode ring and maximum current density are the same as in the previous example, the maximum magnitude of the current through any electrode is ⅓ greater. When the maximum current is passed through one electrode, the return current is divided in various proportions between the other two electrodes. The maximum dipole that can be generated by a ring of three electrodes as a function of θ traces a hexagon 246, similar to that illustrated in FIG. 33. For most orientations of the stimulating field, the magnitude of the maximum dipole generated by a broken ring of three stimulation sites is greater than the dipole generated by a broken ring of four stimulation sites as seen by the square 243 from FIG. 32 superimposed in FIG. 33.

Figure 33:
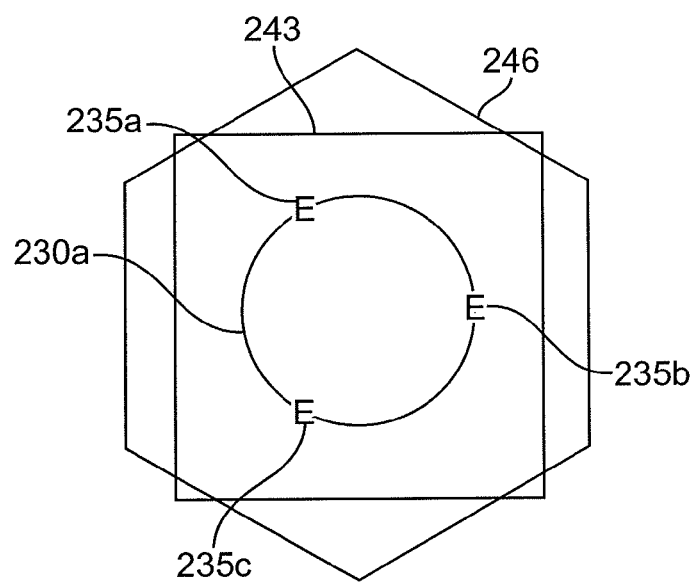
FIG. 33 illustrates a model of the magnitude of a dipole generated by three stimulation sites separated by 120° as compared with the model in FIG. 32.

FIGS. 32 and 33 illustrate a simplified model which clarifies the advantages of using a prime number of stimulation sites such as three. There are three stimulation sites on a broken ring in the preferred embodiment of FIG. 19. FIG. 32 illustrates the case of four electric monopoles 234a, 234b, 234c and 234d arranged at points around a circle 230a. Monopoles 234a and 234c are equally and oppositely charged, and generate a dipole, as do monopoles 234b and 234d. The radial position of points on the square 234 represent the maximum net dipole that can be created by the sum of the two dipoles 234a, 234c and 234b, 234d, subject to the constraint that the maximum charge on a monopole is of magnitude one. The sum of the charge of the four monopoles is zero.

FIG. 33 illustrates the case of three electric monopoles 235a, 235b and 235c arranged at points around a circle 230a. The maximum net dipole square 243 of FIG. 33 is superimposed here for reference. Three electric monopoles generate an oriented dipole more efficiently, as diagrammed by maximum net dipole hexagon. Two dipoles are generated by one monopole of one polarity, and two of the opposite or zero charge. The sum of the charge of all three monopoles is zero. The radial position of points on the hexagon 246 represent the maximum net dipole that can be created by the sum of the two dipoles, subject to the constraint that the maximum charge on any monopole cannot exceed the magnitude 1.2. The larger maximum charge constraint is used here because the surface area of each stimulation site of a fixed axial length is greater if each portion occupies ⅓ of the circumference, than if each portion occupies ¼ of the circumference. The sides of the hexagon nearest the electrodes 235a, 235b, 235c are generated in the situation where the constraining electrodes has positive polarity, and the sides of the hexagon opposite these are generated in the situation when the constraining electrode has negative polarity. It can be seen that the radial position of the hexagon 246 is farther from the origin than the square 243 at most directions from the origin. For a fixed axial extent of the broken ring, three stimulation sites can deliver a larger effective stimulus compared to four stimulations sites. Alternatively, for a fixed effective stimulus, the axial length of a broken ring of 3 stimulation sites can be shorter than for a broken ring of 4 stimulation sites. The preferred embodiment of the invention has the advantage over other probes of supporting better steerability of the electric current for the situation in which the maximum current density is constrained. This description of the invention does not preclude using a stimulation protocol in which stimulation sites on different broken rings are stimulated simultaneously or in coordination.

It will be apparent to those skilled in the art that a stimulating probe with a broken ring of 6 stimulation sites (or any other multiple of 3) can be used in a manner so as to obtain the advantages of this invention. This may be accomplished by controlling the ring of six stimulation sites as three stimulation sites, each comprised of a pair of adjacent stimulation sites.

Therefore, at any axial position, the number of stimulation sites is a prime number. A prime number yields more combinatorial possibilities for simultaneously using all electrode surfaces to achieve different stimulation orientations. Using all electrode surfaces keeps current density as low as possible. In a preferred embodiment, the number of stimulation sites is 3. In another embodiment, the number of stimulation sites is 5. Configurations with 2, 5 or 7 stimulation sites could achieve the current density advantages which this invention seeks to achieve also, although to a lesser degree.

Figure 19:
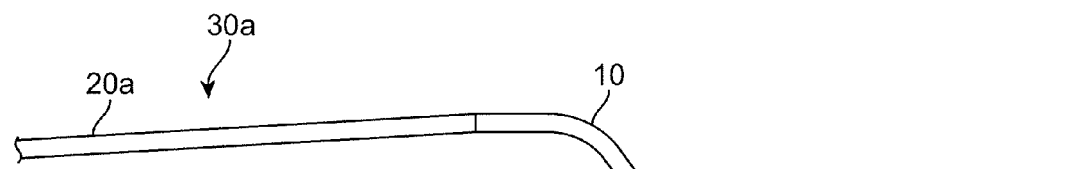
FIG. 19 illustrates one embodiment of a tissue monitoring and modulation lead.

Referring now to FIG. 19, a tissue modulating and monitoring probe is illustrated. FIG. 19 shows a preferred embodiment of the probe. It is a cylindrical probe, with a flexible probe body 10 and an optional multiple contact connecting terminal 20a. Additional details on multiple contact connecting terminals are disclosed above. Other connectors may be used and are well known in the art. At the distal end of the probe 30a there are one or more broken annular rings of stimulating sites. The stimulating sites may be aligned with matching angular position on all rings, or may be offset to different angular positions on different rings. There are also one or more circumferential electrode bands suitable for recording local field potentials, and a recording electrode at or near the most distal point. In this preferred embodiment, the maximum diameter of the multiple contact terminal 20a is the same as the diameter of the flexible probe body 10.

In this embodiment, at four axial positions, three stimulation sites 33a, 33b, 33c, 34a, 34b, 34c, 35a, 35b, 35c, 36a, 36b, 36c are arranged as broken rings, for a total of 12 stimulation sites. These are better seen in the cross-sectional views of FIGS. 23-30. Also in this embodiment are three recording bands 37, 38, 39 arranged in the gaps between the broken rings. The size of the recording sites is suitable for recording local field potentials, with an exposed area ranging from about 0.0005 $mm^2$ to about 0.5 $mm^2$ but the area could be up to about 0.8 $mm^2$. Some embodiments have smaller recording sites that improve extracellularly recordings of action potentials. Such recording sites range in exposed area from about $1.9 \times 10^{-5}$ $mm^2$ to about 0.002 $mm^2$, but they could be as large as about 0.1 $mm^2$. The form of the recording sites could be the bare end of an insulated wire, a thin film, a metal pad, or an insulated region with a portion of the insulation removed to expose an electrical conductor within the wall of the device. Alternative embodiments may have no recording rings, or may have more recording rings. Additional recording rings or point electrodes may be located along the probe body 10 or at the probe tip 32. The embodiment does not restrict the alignment of the recording electrodes (bands and/or points) with respect to the stimulation sites.

There must be a nonconductive gap of at least 100 μm between stimulating and recording surfaces, and between recording surfaces, to reduce shunting and improve the isolation of the recorded signals. It is desirable that electrical signals traversing through the probe do not interfere with each other. It is especially desirable that the high level electrical stimulation signals not interfere with the low level recording signals. Therefore, it is preferable that the conductors carrying recording signals lay in an inner helix, while conductors carrying stimulation signals lay in an outer helix. The pitch of the two helices may be the same or may be different, so that no pair of stimulation and recording conductors traverse adjacent paths for an appreciable distance. This minimizes capacitive coupling between any stimulating conductors and any recording conductors. In other embodiments, a conductive coating may be applied to the outside of the helix of recording conductors. This can be grounded to decrease electromagnetic interference between the two types of conductors. In yet another embodiment, a metal foil, which may be grounded, is wrapped between the inner and outer wire helices.

In other embodiments, the conductors carrying recorded signals lay between conductors carrying electrical stimulation signals. This embodiment has the advantage that the conductors lay in a single lamina and can be more compact and more flexible, although in some instances this embodiment may have the disadvantage that when stimulating current modulates a stimulating conductor, the stimulation signal may couple into adjacent recording conductors. Note that not all of the stimulus conductors are required to carry a current at any instant. In many uses of the probe, some of the recording conductors will therefore be well separated from active stimulating conductors at any instant. In another embodiment, the stimulating wires and recording wires course as adjacent groups of conductors in a helix.

The wires should be mechanically strong and electrically conductive. Suitable materials include alloy MP35N (cobalt chrome alloy), stainless steel, and tungsten or tungsten alloy wire which has been gold plated to facilitate continuity with the stimulation sites and to the extra-cranial connector. It is important that the material be minimally magnetic to maximize MRI compatibility.

Stimulation sites are made of a relatively inert material which maximizes safe charge transfer, such as platinum, iridium or an alloy of platinum and iridium. The body of the probe is coated by a biocompatible polymer, such as silicone rubber or polyurethane, which supports bending with a short radius of curvature where the probe exits the cranium.

Figure 20:
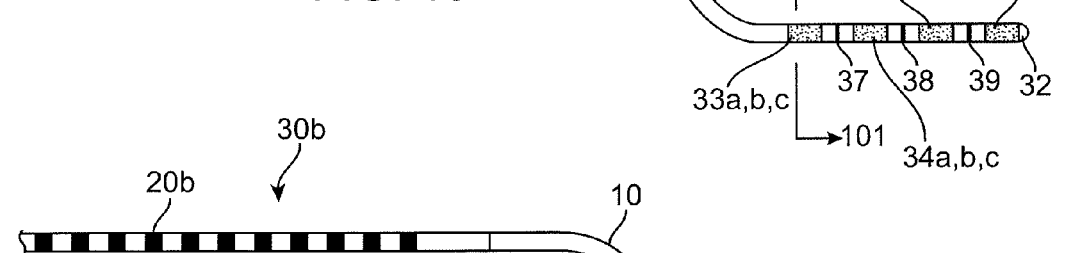
FIG. 20 illustrates another embodiment of a tissue monitoring and modulating lead.

FIG. 20 illustrates an alternative embodiment of the probe 30b. Probe 30b is similar to the probe 30a of FIG. 19 except that it adds ports 40 which may permit chemical substances to enter or leave the probe lumen. The ports 40 may be covered by a semi-permeable membrane. Alternatively a chemically controlled gating mechanism, such as a chemically reactive hydrogel, may be placed near the ports. Such a hydrogel can swell or contract depending upon the chemical composition of the adjacent medium. The gating mechanism may operate based on bulk swelling and occlusion of the port, or the hydrogel may be formed with a mechanical accessory structure. An example of such as structure includes a bimorph beam as described by R. Bashir, J. Z. Hilt, O. Elibol, A. Gupta, and N. A. Peppas in "Micromechanical Cantilever as an Ultrasensitve pH Microsensor," published in Applied Physics Letters, 81(16):3091-3093, 2002. Another example includes a surface covering fenestrated with microports as disclosed by A. Baldi, M. Lei, Y. Gu, R. A. Siegel and B. Ziaie in an article entitled "A Microstructured Silicon Membrane with Entrapped Hydrogels for Environmentally Sensitive Fluid Gating," published in Sensor and Actuators B, 114(1):9-18, 2006, or another example includes a pad which displaces elements suited to forming an occlusive seal as described by A. Baldi, Y. Gu, P. E. Loftness, R. A. Siegel and B. Ziaie in "A Hydrogel-Actuated Environmentally Sensitive Microvalve for Active Flow Control," published in the Journal of Microelectromechanical Systems, 12(5):613-621, 2003. The entire contents of these references are incorporated herein by reference.

Since the hydrogels may be formulated such that their volume has different chemical dependencies, different hydrogels may be associated with ports at different pre-determined positions on the lead, so that drugs may be delivered selectively to pre-determined positions on the probe. Likewise, samples of the extra-cellular space or cerebral spinal fluid (CSF) may be obtained from pre-determined positions on the probe. Examples of chemical gating mechanisms that are controlled directly by pH include those described previously in "Micromechanical Cantilever as an Ultrasensitve pH Microsensor. Gating mechanisms controlled by the presence of carbon dioxide via a relationship to pH include those described by R. Steege, H. Sebastiaan, W. Olthuis, P. Bergveld, A. Berg, and J. Kolkman in "Assessment of a New Prototype Hydrogel CO2 Sensor; Comparison with Air Tonometry," as published in The Journal of Clinical Monitoring and Computing 21(2):83-90, 2007. Other examples of gating mechanisms controlled by the presence of glucose are disclosed by Theeuwes et al. in U.S. Pat. No. 6,997,922. The entire contents of the above listed references are incorporated herein by reference.

Figure 21:
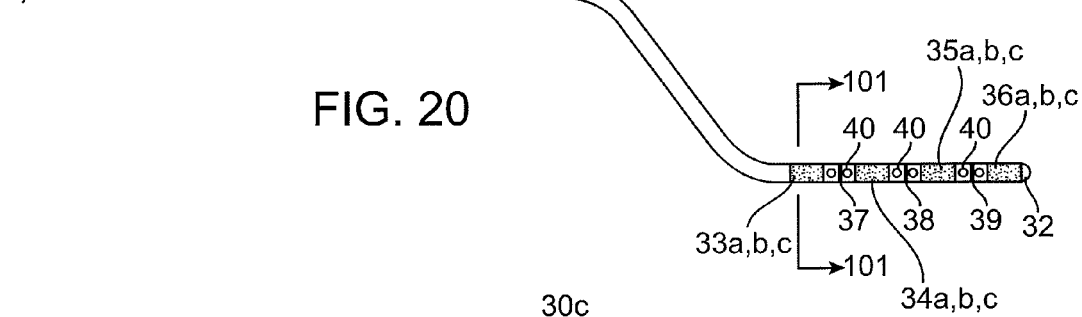
FIG. 21 illustrates yet another embodiment of a tissue monitoring and modulating lead.

FIG. 21 illustrates an alternative embodiment of probe 30c in which the probe tip 32a is electrically conductive, serving as an additional stimulation site. This could serve as a conventional stimulation site, supporting monopolar and bipolar stimulation. In conjunction with a distal ring of stimulation sites 36a-c it forms a group of stimulation sites centered on the vertices of a tetrahedron, supporting steering of the current near the tip in three dimensions. The embodiment of FIG. 21 also has an additional recording electrode 42 between stimulating electrodes 36a-36c and distal stimulating electrode 32a. Also, multiple contact connecting terminal 20c has a plurality of electrical contacts axially spaced along two hemi-cylidrical or D-shaped connectors, as previously disclosed.

Figure 22:
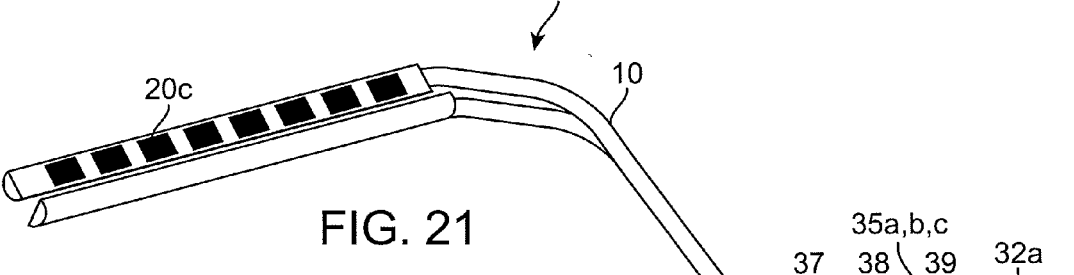
FIG. 22 illustrates still another embodiment of a tissue monitoring and modulating lead.

FIG. 22 illustrates an alternative embodiment of the probe, 30d, demonstrating that the multiple contact terminal 20d need not have the same diameter as the probe body 10. Here, contact terminal 20d is a larger diameter cylindrical shaped plug with receptacles for coupling the probe 30d with the rest of the monitoring and modulation system. This embodiment illustrates that the surface of recording electrodes need not be circular, but may be configured as recording points 43. Alternative embodiments may include multiple recording sites, some configured as rings, and other configured as points. In other embodiments the recording electrodes may take other shapes, including squares, rectangles or irregular shapes. In yet another alternative embodiment, the multiple contact terminal may allow for a lumen or conduit for the passage fluid within the probe. Fluid may pass in one or more lumens, and may flow into or out of the brain, or both.

Figure 23:
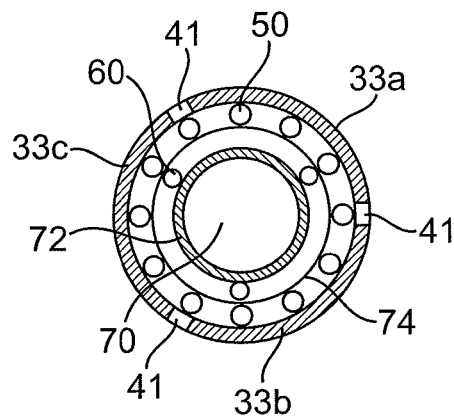
FIG. 23 illustrates a cross-section of a tissue monitoring and modulation lead.

FIG. 23 illustrates an axial cross-sectional view of a preferred embodiment, at section line 101 in FIG. 19. In the preferred embodiment the central lumen 70 is surrounded by a tube 72 made of a biocompatible polymer, such as polyurethane, silicone rubber or polyamide. In alternative embodiments the lumen is a polymer coating, and the insulated recording conductors 60 may reside in the inner lumen. Recording conductors 60 are wound in a helix from the recording sites to their termination at the contact terminal 20. Likewise, the stimulating conductors 50 are wound in a helix from the stimulation sites to their termination at the contact terminal 20. In a preferred embodiment, the stimulating conductors 50 have larger size than the recording conductors 60 because resistive losses are a greater concern for the stimulating conductors 50, but all conductors may be of the same or similar dimension in alternative embodiments. In a preferred embodiment, the pitches of the recording wire helix and the stimulating wire helix are different, to decrease the average capacitive coupling between the wires. In alternative embodiments the helices could have the same pitch. The two helices may have the same or opposite orientation (one clockwise, the other counterclockwise). Conductors 50, 60 are embedded in a flexible polymer, and are insulated in the preferred embodiment, but could or could not rely on the surrounding polymer for insulation in an alternative embodiment. In the preferred embodiment, a layer of electrically conductive material 74 is interposed between the recording and stimulating conductors, which may be attached to a low impedance electrical reference. Alternative embodiments may use layer 74 or the central lining of the central lumen 72 as an internal stimulating electrode. Alternative embodiments may omit this layer 74 to simplify manufacturing. Stimulation sites 33a-c lay on the surface of the probe, with gaps of nonconductive material 41 between them. The stimulation sites 33a-c may be of the form of sections of a tube adhered to the probe, and welded or riveted to the conductors 50, or may be fabricated with thin film technology. Examples of thin film technology that could be used to fabricate the probe are described, for example, in U.S. Pat. Nos. 7,051,419 and 7,047,082 the entire contents of which are incorporated herein by reference. The conductors 50, 60 in FIG. 23 are shown as having a circular profile to suggest transversely cut round wires, but alternative forms could use shaped wires such as those having a square, rectangular or elliptical cross-section, or thin film technologies may be used for the conductors. FIG. 23 shows 12 stimulating conductors 50 and 3 recording conductors 60 corresponding to the preferred embodiment, but alternative embodiments could have more or fewer conductors to support various numbers of electrodes.

Figure 24:
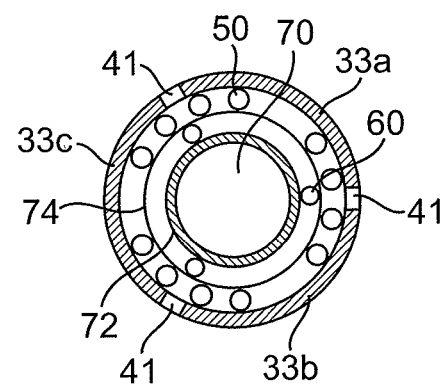
FIG. 24 shows a cross-section of an alternative embodiment of a monitoring and modulation lead.

FIG. 24 illustrates an alternative embodiment, in which the stimulating conductors 50 are arranged in groups rather than uniformly spaced around the circumference of the probe. Three groups of four are illustrated, but alternatively the conductors could be arranged in 4 groups of three. Such embodiments could allow for ports communicating between the central lumen 70 and the outside of the probe, or for improved flexibility of the probe in conjunction with reduced wall thickness between groups of conductors.

Figure 25:
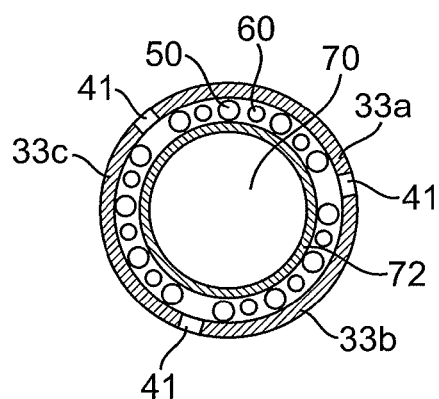
FIG. 25 shows a cross-section of yet another embodiment of a monitoring and modulation lead.

FIG. 25 illustrates an axial cross-sectional view of an alternative embodiment, at section line 101 in FIG. 19. In this embodiment, the stimulating and recording conductors are in the same annular space of the probe, unlike prior embodiments where the conductors are separated. Because this embodiment places both conductors in the same annular space, the central lumen 70 may be larger. In a preferred embodiment the stimulating conductors 50 and recording conductors 60 alternate around the helix, but in alternative embodiments the stimulating conductors and recording conductors could course as separate groups. In alternative embodiments, there may be additional conductors between the stimulating 50 and recording 60 conductors, which may be connected to the point of electrical neutrality. In alternative embodiments, the tube 72 may be coated with an electrically conductive material, which may be connected to the point of electrical neutrality.

Figure 26:
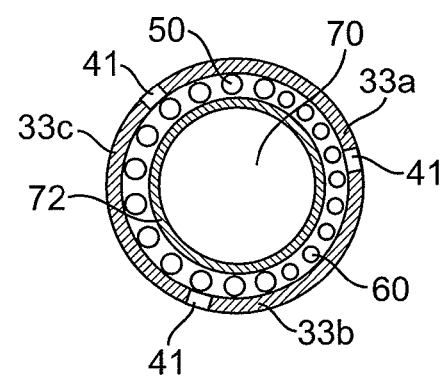
FIG. 26 shows a cross-section of still another embodiment of a monitoring and modulation lead.

FIG. 26 illustrates an alternative embodiment wherein the recording conductors 60 and stimulating conductors 50 are separated into groups. This embodiment has the advantage of reduced opportunities for undesirable capacitive coupling between stimulating and recording conductors compared to the embodiment illustrated in FIG. 25, but increases the opportunities for undesirable capacitive coupling between separate recording conductors.

Figure 27:
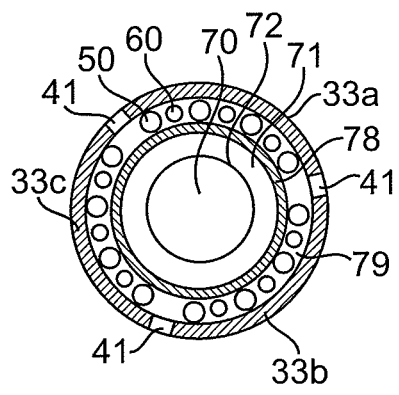
FIG. 27 shows another cross-section of another embodiment of a monitoring and modulation lead.

FIG. 27 illustrates an embodiment with dual lumens, central 70 and annular 71, to permit delivery or sampling of a fluid (gas or liquid) substance or drug, or sampling of a liquid or volatile substance. The lumens may communicate with ports, shown as 40 in FIGS. 20 and 31A-31, and such communication may be electrically or chemically gated. The distal ends of the lumens may be closed, permeable, selectively permeable, or open, to release the lumen contents or some fraction or portion of the lumen contents. The distal ends of the two lumens may communicate with each other, so that one delivers a liquid containing a drug such a levodopa, or a gaseous medium with bioactive effects such as carbon monoxide or nitrous oxide, and another lumen retrieves the medium, after an opportunity to exchange substance or substances with the medium near ports 40 or other openings in the probe. Other therapeutic agents that may be delivered are well known in the art, such as those disclosed in U.S. Pat. Nos. 6,094,598 and 6,227,203 both of which, the entire contents are incorporated herein by reference and often, extracellular fluid such as cerebral spinal fluid (CSF) is sampled. In this embodiment, conductors for electrical stimulating and recording course together within an additional annulus 79 created by an additional wall 78 in the probe.

Figure 28:
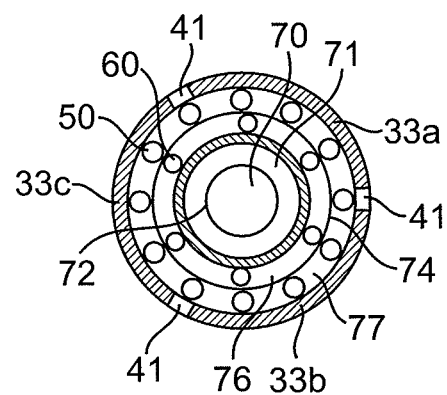
FIG. 28 shows yet another cross-section of an embodiment of a monitoring and modulation lead.

FIG. 28 illustrates an arrangement similar to that in FIG. 27, except that the conductors for stimulating and recording course through two separate annular rings 76 and 77, both concentric to the inner two lumens 70 and 71. In other embodiments, there may be more than two lumens, and the lumens need not be concentric.

Figure 29:
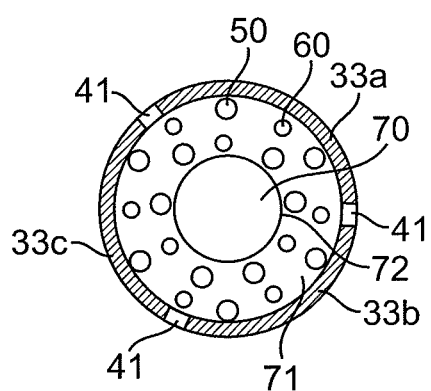
FIG. 29 shows still another cross-section of another embodiment of a monitoring and modulation lead.

FIG. 29 illustrates an arrangement similar to that in FIG. 27, except that there is a single lumen 72. Additionally, conductors 50 and 60 are randomly oriented and therefore may allow the probe to be more easily fabricated as opposed to a probe with conductors in a defined pattern.

Figure 30:
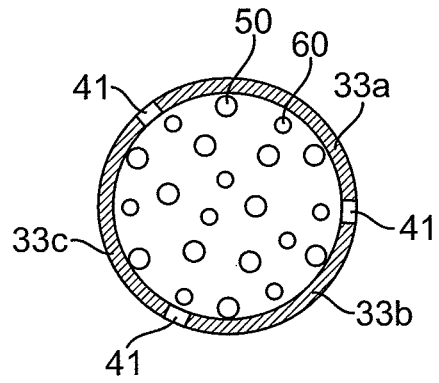
FIG. 30 shows another cross-section of another embodiment of a monitoring and modulation lead.

FIG. 30 illustrates an arrangement with no lumen for either a guide wire, or for supporting mass transfer. The conductors course together through the center of the probe.

Figure 31A:
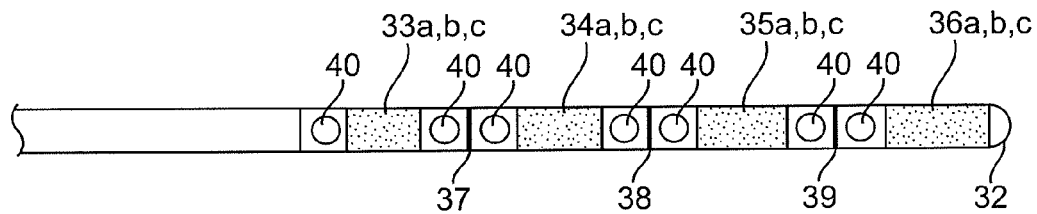
FIGS. 31A-31C highlight the recording and stimulating regions of an exemplary embodiment of a monitoring and modulation lead.
Figure 31B:
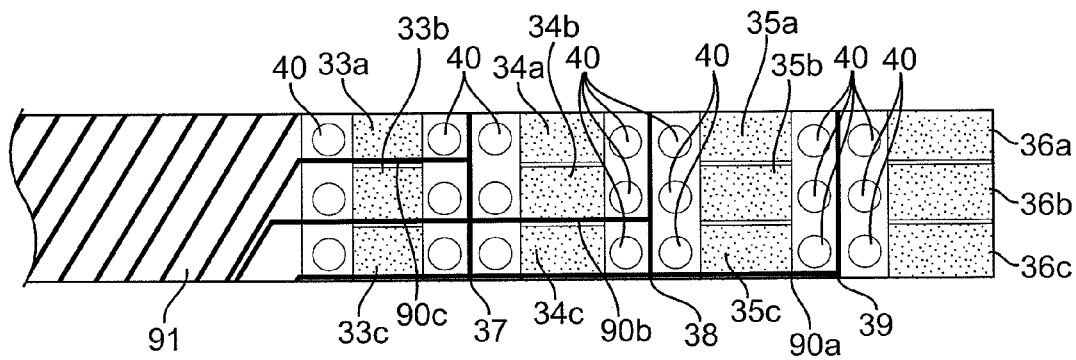
Figure 31C:
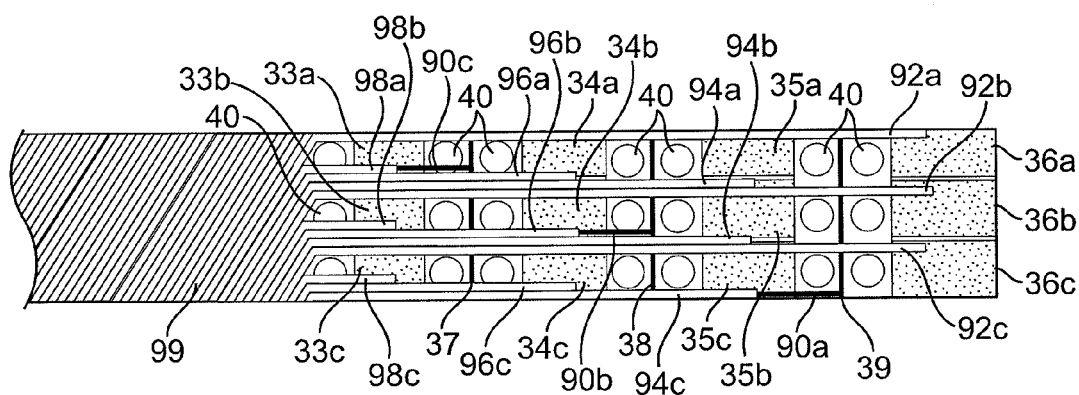

FIGS. 31A-31C illustrate an arrangement for the stimulating and recording conductors, similar to the embodiments illustrated in FIG. 20. FIG. 31A shows a probe having four regions of stimulating electrodes 36a-36c, 35a-35c, 34a-34c and 33a-33c, with each region having three independent stimulation sites. Additionally, the probe in FIG. 31A has recording electrodes 37, 38 and 39 as well as ports 40. The probe of FIG. 31A is shown in FIGS. 31B-31C with the circumference of the probe unwrapped, such that the upper edge and the lower edge of the conductors are actually continuous with each other. In the region of the probe tip, the conductors course in the axial direction, and turn to form helical windings along the probe body. FIG. 31B shows the recording electrode conductors 90a, 90b and 90c coursing in the axial direction near the probe tip and then turning to form helical windings along the probe body. FIG. 31C illustrates a similar pattern for stimulating electrode conductors 92a, 92b, 92c, 94a, 94b, 94c, 96a, 96b, 96c and 98a, 98b, 98c.

Figure 34:
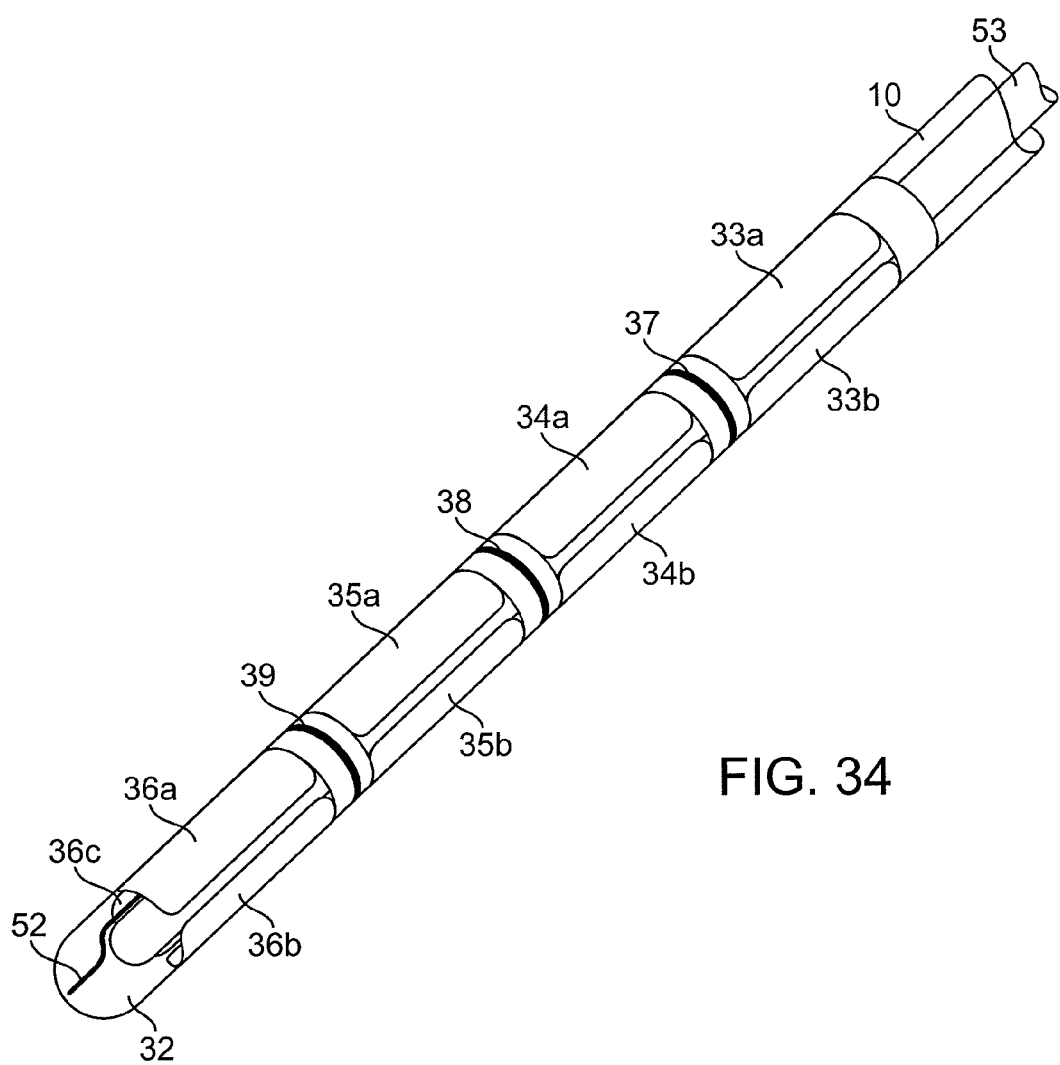
FIG. 34 shows a perspective view of an embodiment of a brain monitoring and modulation lead.

FIG. 34 shows a perspective view of a monitoring and modulation lead. In FIG. 34, four stimulation regions on the lead each contain three independent stimulation electrodes. All three stimulation electrodes 36a, 36b, 36c are only visible on the distal-most region. Two stimulating electrodes are visible in the other regions of the lead including 35a, 35b, 34a, 34b, 33a, 33b. Additionally, the lead has three recording electrodes 37, 38 and 39 as well as an additional recording electrode 52 near the distal lead tip 32. An inner shaft 53 is contained within lead body 10 and may be adapted to accommodate guidewires, stylets, lumens, etc. previously described herein.

Table 1 below summarizes data collected that demonstrate that different functional stimulation effects can be achieved by stimulating different stimulation sites around an annular ring. A lead similar to that illustrated in FIG. 34 was inserted into the basal ganglia of an anesthetized cat. The stimulating sites in the most distal annular ring (36a, 36b and 36c) were energized together and independently to electrically stimulate the brain. The ground was placed in the temporalis muscle. Electrical stimulation of sufficient magnitude evoked a response in either the ipsilateral or contralateral or both facial muscles. Stimulation magnitude was delivered in voltage steps, and the motor response was graded on a rank-ordered scale (NR—No Response; THR, Response Threshold; larger numbers correspond to larger magnitude of suprathreshold responses). When site 36a was stimulated alone, the response threshold for ipsilateral movement was lower than for contralateral movement. When site 36b was stimulated alone, the response threshold for ipsilateral and contralateral movement was the same. When site 36c was stimulated alone, the threshold for contralateral movement was lower than for ipsilateral movement. When all three sites were stimulated simultaneously, the threshold for ipsilateral movement was lower than for contralateral movement, but the threshold for both ipsilateral and contralateral movement was lower than with stimulation of any single site. Data from this testing is summarized in Table 1 below, and this pattern of differential stimulation thresholds demonstrates that stimulating different sites within an annular ring steers electrical current within the brain.

Figure 35A:
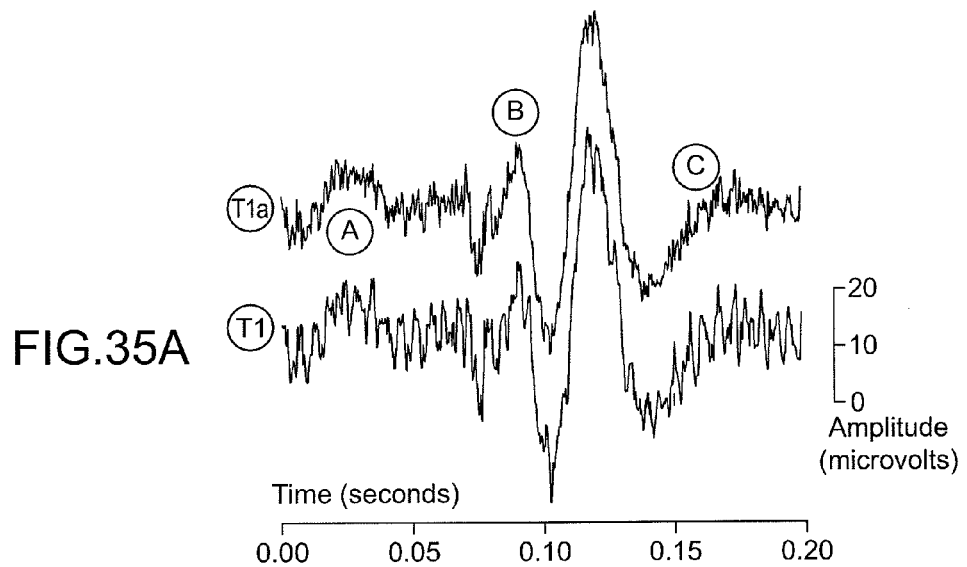
FIGS. 35A-35C show sample recordings of brain electrical potentials from two recording electrodes.
Figure 35B:
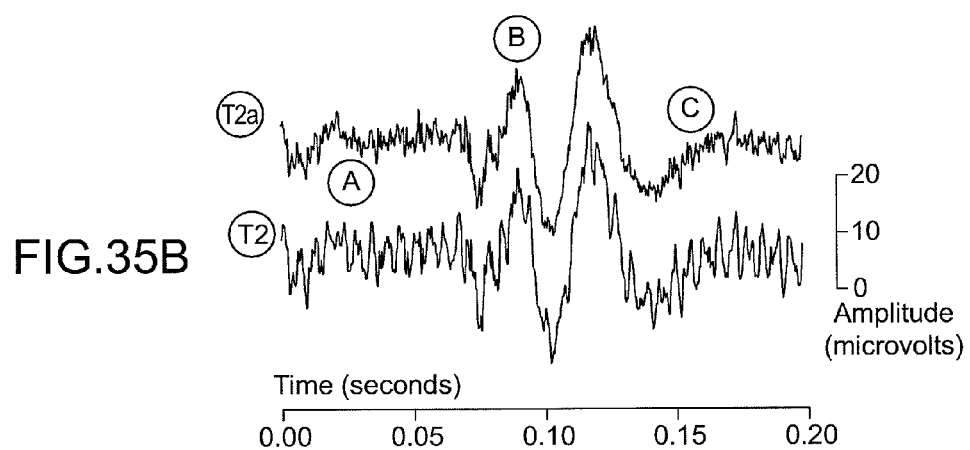
Figure 35C:
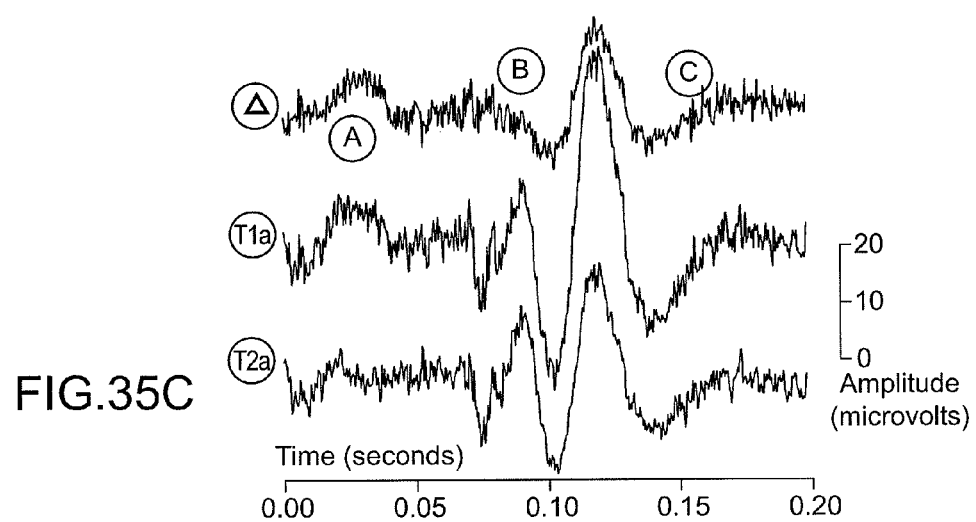

FIGS. 35A-35C demonstrate that the lead can record field potentials, and that different recording sites record different potentials. The recording was obtained from the same lead illustrated in FIG. 34 as discussed above, and with the same placement. The response was evoked by sensory stimulation of the visual pathways by waving a flashlight before the eyes. In FIGS. 35A, Trace T1 was recorded from recording site 38, and in FIG. 35B trace T2 was recorded from recording site 39. Spectrum analysis of these traces revealed oscillations at 180 Hz, and 300 Hz, which are believed to result from unintended coupling to the power grid. A Christiano-Fitzgerald filter was applied to remove signal energy near these frequencies, and the filtered traces are denoted T1a and T2a as shown in FIGS. 35A-35C. The trace Δ in FIG. 35C is the arithmetic difference T1a-T2a. The traces look similar, but they are not proportional, as they would be if they resulted principally from electrical cross-talk. At position A, T1/T1a has a more sustained positivity compared to T2/T2a. At position B, the positivity in traces T1/T1a and T2/T2a are nearly identical. The amplitude of the triphasic wave between positions B and C differs considerably in traces T1/T1a and T2/T2a. The amplitude of this recorded potential is somewhat less than the amplitude of an optimally recorded field potential, reflecting the position of the lead near but not in the optic tract.

Figure 36A:
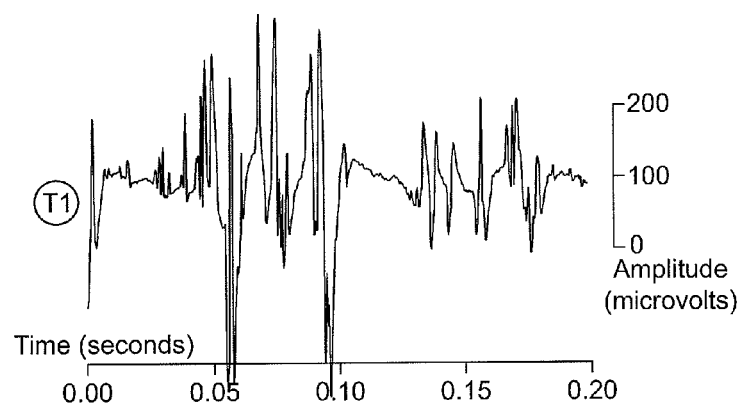
FIGS. 36A-36C show additional sample recordings of brain electrical potentials from two recording electrodes.
Figure 36B:
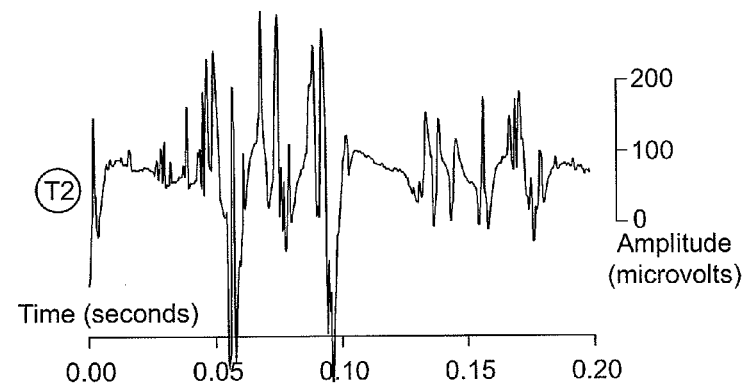
Figure 36C:
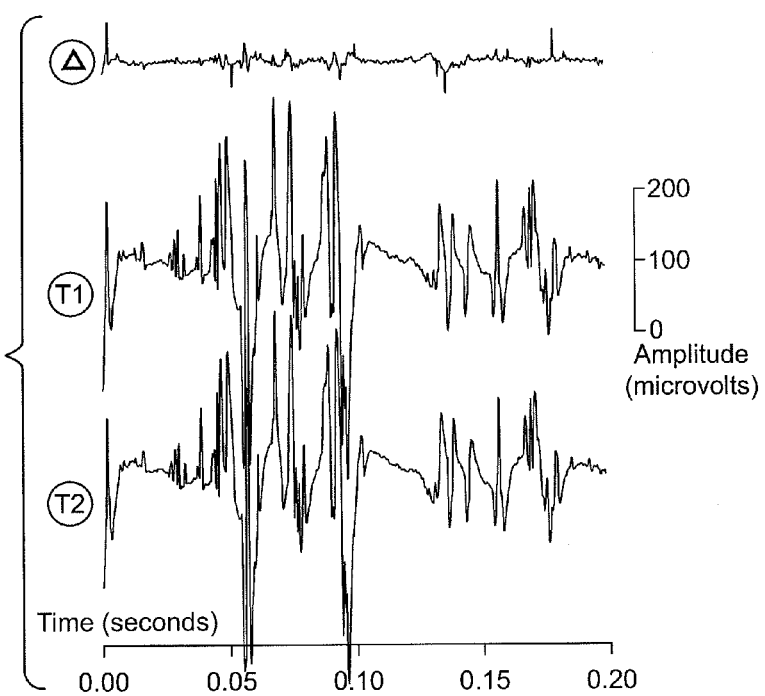

FIGS. 36A-36C demonstrate that the lead can record spontaneous activity field potentials characteristic of placement in a grey matter nucleus. The recording was obtained from a location 3 mm dorsal to the location from which the recording in FIGS. 36A-36C was obtained. Because the amplitude of this recording was much greater than the amplitude of interference from the power grid, Christiano-Fitzgerald filtering was not necessary. Trace T1 in FIG. 36A was recorded from recording site 38, and trace T2 in FIG. 19B was recorded from recording site 39. The trace A in FIG. 19C is the arithmetic difference T1-T2. The traces look similar, with a time course and amplitude characteristic of field potential recordings. The difference trace, A, has several transient waves with duration from 0.5 to 3.5 msec, and amplitude of a few tens of millivolts, characteristic of action potential waveforms. Together with the recording shown in FIGS. 35A-35C, these data demonstrate that a lead such as that illustrated in FIG. 34 can record field potentials from white matter and grey matter, and with suitable signal processing can also record action potential spikes.

TABLE 1

| Activated Surfaces | Stimulation (V) | Ipsilateral Facial Muscle Response Grade | Contralateral Facial Muscle Response Grade |
|---|---|---|---|
| 36a, 36b, 36c | 1.0 | NR | NR |
| | 2.0 | NR | NR |
| | 2.2 | THR | NR |
| | 2.6 | 1 | NR |
| | 2.7 | 1 | THR |

TABLE 1-continued

| Activated Surfaces | Stimulation (V) | Ipsilateral Facial Muscle Response Grade | Contralateral Facial Muscle Response Grade |
|---|---|---|---|
| 36a | 1.0 | NR | NR |
| | 2.0 | NR | NR |
| | 3.0 | NR | NR |
| | 3.6 | THR | NR |
| | 4.0 | 1 | NR |
| | 4.3 | 1 | NR |
| | 4.5 | 2 | THR |
| 36b | 1.0 | NR | NR |
| | 2.0 | NR | NR |
| | 2.4 | THR | THR |
| | 4.0 | 2 | 2 |
| 36c | 1.0 | NR | NR |
| | 2.0 | NR | NR |
| | 3.0 | NR | NR |
| | 3.5 | NR | THR |
| | 4.0 | THR | 1 |
| | 4.5 | 1 | 1 |
| | 5.0 | 2 | 2 |

While the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. A system for stimulating tissue, said system comprising:
   a connector comprising a male connector and a female connector having one or more channels axially disposed therein, wherein at least one of the channels has an indexing element adapted to receive the male connector in a defined orientation relative to the female connector, thereby forming at least two electrical connections along two or more axial positions when the male connector is disposed in the female connector;
   a medical lead comprising an elongate member having a proximal end, a distal end, and a plurality of annular stimulating regions axially arranged along the elongate member adjacent the distal end thereof, wherein at least one of the annular stimulating regions consists essentially of at least three independent stimulation electrodes equally spaced apart from one another and separated from one another by an insulator so that each stimulation electrode may be stimulated independently of the other stimulation electrodes, the at least of the annular stimulating regions completely surrounding a circumference of the elongate member, wherein the medical lead is electrically coupled with the male or the female connector; and
   an anchoring device, the anchoring device adapted to removably fix the medical lead to a patient's head.

2. The system of claim 1, wherein the medical lead further comprises a plurality of recording electrodes disposed adjacent the stimulating electrodes, the recording electrodes being adapted to measure local tissue potentials.

3. The system of claim 2, further comprising a plurality of conductors helically wound around the elongate shaft and electrically coupled with the recording electrodes.

4. The system of claim 1, wherein the elongate member further comprises a lumen extending at least partially between the proximal and distal ends thereof, the lumen adapted to slidably receive a guidewire or stylet.

5. The system of claim 1, further comprising a plurality of conductors helically wound around the elongate member and electrically coupled with the electrodes.

6. The system of claim 1, wherein the medical lead and connector are compatible with magnetic resonance imaging.

7. The system of claim 1, further comprising a pulse generator, the pulse generator adapted to provide an electrical stimulus to the tissue via the stimulating electrodes.

8. The system of claim 1, further comprising a lead extension, wherein the medical lead is coupled with the male or the female connector, and wherein the remaining connector is coupled with the lead extension.

9. A system for stimulating tissue, said system comprising:
a connector a comprising a male connector and a female connector having one or more channels axially disposed therein, wherein at least one of the one or more channel has an indexing element adapted to receive the male connector in a defined orientation relative to the female connector, thereby forming at least two electrical connections along two or more axial positions when the male connector is disposed in the female connector; and
a medical lead comprising an elongate member having a proximal end, a distal end, and a plurality of annular stimulating regions axially arranged along the elongate member adjacent the distal end thereof, wherein at least one of the annular stimulating regions consists essentially of at least three independent stimulation electrodes equally spaced apart from one another and separated from one another by an insulator so that each stimulation electrode may be stimulated independently of the other stimulation electrodes, the at least one of the annular stimulating regions completely surrounding a circumference of the elongate member,
wherein the medical lead is electrically coupled with the male or the female connector,
wherein the elongate member further comprises a lumen extending at least partially between the proximal and distal ends thereof, the lumen adapted to slidably receive a guidewire or stylet,
wherein the elongate member further comprises one or more ports near the distal end thereof, the ports in fluid communication with the lumen and adapted to deliver a therapeutic agent to and/or to receive a chemical substance from the tissue.

10. The system of claim 9, wherein the system comprises levodopa, and the therapeutic agent comprises the levodopa.

11. The system of claim 9, wherein the one or more ports comprise a gating member adapted to permit selective enablement of the ports.

12. The system of claim 9, wherein the medical lead and connector are compatible with magnetic resonance imaging.

13. The system of claim 9, further comprising a plurality of conductors helically wound around the elongate member and electrically coupled with the electrodes.

14. The system of claim 9, wherein the elongate member further comprises a lumen extending at least partially between the proximal and distal ends thereof, the lumen adapted to slidably receive a guidewire or stylet.

15. A system for stimulating tissue, said system comprising:
a connector comprising a male connector and a female connector having one or more channels axially disposed therein, wherein at least one of the one or more channels has an indexing element adapted to receive the male connector in a defined orientation relative to the female connector, thereby forming at least two electrical connections along two or more axial positions when the male connector is disposed in the female connector;
a medical lead comprising an elongate member having a proximal end, a distal end, and a plurality of annular stimulating regions axially arranged along the elongate member adjacent the distal end thereof, wherein at least one of the annular stimulating regions consists essentially of at least three independent stimulation electrodes equally spaced apart from one another and separated from one another by an insulator so that each stimulation electrode may be stimulated independently of the other stimulation electrodes, the at least one of the annular stimulating regions completely surrounding a circumference of the elongate member, wherein the medical lead is electrically coupled with the male or the female connector;
a pulse generator, the pulse generator adapted to provide an electrical stimulus to the tissue via the stimulating electrodes; and
a patient programmer, the programmer being adapted to control the pulse generator.

16. The system of claim 15, wherein the medical lead and connector are compatible with magnetic resonance imaging.

17. The system of claim 15, further comprising a plurality of conductors helically wound around the elongate member and electrically coupled with the electrodes.

18. The system of claim 15, wherein the elongate member further comprises a lumen extending at least partially between the proximal and distal ends thereof, the lumen adapted to slidably receive a guidewire or stylet.

* * * * *